(12) United States Patent  (10) Patent No.: US 8,082,809 B2
Luellen et al.  (45) Date of Patent: Dec. 27, 2011

(54) COMBINE HARVESTER AND ASSOCIATED METHOD FOR SELECTIVELY GATHERING GRAIN TEST DATA

(75) Inventors: Ty T. Luellen, Minburn, IA (US); Douglas R. Peirce, Pleasant Hill, IA (US); Lyndon J. Schroeder, Urbandale, IA (US); Barry L. Stott, Winterset, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 12/900,113

(22) Filed: Oct. 7, 2010

(65) Prior Publication Data

US 2011/0086684 A1   Apr. 14, 2011

Related U.S. Application Data

(60) Provisional application No. 61/249,914, filed on Oct. 8, 2009.

(51) Int. Cl.
  *G01N 1/20*  (2006.01)
(52) U.S. Cl. .................................................. 73/863.41
(58) Field of Classification Search ......... 73/73, 863.21, 73/863.51, 863.56, 863.58, 863.54, 863.83, 73/863.53, 863.41; 56/10.2 B; 702/129, 702/156; 324/689, 664, 688; 460/7, 1, 149, 460/114, 79
See application file for complete search history.

(56) References Cited

U.S. PATENT DOCUMENTS

| 2,467,791 | A | * | 4/1949 | Welty et al. ................. 73/863.21 |
| 4,611,605 | A | | 9/1986 | Hall et al. |
| 4,663,978 | A | * | 5/1987 | Lenski et al. ............... 73/863.52 |
| 4,821,744 | A | | 4/1989 | Turner et al. |
| 4,896,795 | A | * | 1/1990 | Ediger et al. ..................... 222/63 |
| 5,059,154 | A | * | 10/1991 | Reyenga ........................ 460/102 |
| 5,092,819 | A | | 3/1992 | Schroeder et al. |
| 5,106,339 | A | | 4/1992 | Braun et al. |
| 5,173,079 | A | | 12/1992 | Gerrish |
| 5,327,708 | A | * | 7/1994 | Gerrish ............................... 56/1 |
| 5,489,239 | A | | 2/1996 | Matousek et al. |
| 5,751,421 | A | * | 5/1998 | Wright et al. ................. 356/328 |
| 5,890,961 | A | * | 4/1999 | Behnke et al. ..................... 460/6 |
| 5,957,773 | A | * | 9/1999 | Olmsted et al. ................... 460/7 |
| 5,991,025 | A | * | 11/1999 | Wright et al. ................. 356/328 |
| 6,083,103 | A | * | 7/2000 | Posselius et al. ............. 460/114 |
| 6,119,531 | A | | 9/2000 | Wendte et al. |
| 6,121,782 | A | * | 9/2000 | Adams et al. ................. 324/689 |

(Continued)

OTHER PUBLICATIONS

International Search Report and Written Opinion from corresponding International Appl. No. PCT/US2010/052034, mailed Jan. 11, 2011.

*Primary Examiner* — Arpad Fabian-Kovacs
(74) *Attorney, Agent, or Firm* — Alston & Bird LLP

(57) ABSTRACT

The present invention provides a novel combine harvester and associated method configured for gathering grain test data. In general, the combine harvester includes a grain diverting assembly that is configured to selectively divert grain from a grain harvesting path to a grain testing path for the purpose of gathering the grain test data. In various embodiments, the present invention may return the tested grain to the grain harvesting path for further delivery to a primary grain hopper. The present invention may also provide a sampling cup and sample delivery system that allows a sample of the diverted grain to be automatically gathered and delivered to a combine harvester operator location.

34 Claims, 22 Drawing Sheets

U.S. PATENT DOCUMENTS

| | | |
|---|---|---|
| 6,242,927 B1 * | 6/2001 | Adams et al. ............... 324/664 |
| 6,327,899 B1 | 12/2001 | Diekhans et al. |
| 6,358,142 B1 | 3/2002 | Imel et al. |
| 6,412,260 B1 | 7/2002 | Lukac et al. |
| 6,442,916 B1 | 9/2002 | Pope |
| 6,460,008 B1 * | 10/2002 | Hardt ............... 702/156 |
| 6,584,424 B2 * | 6/2003 | Hardt ............... 702/129 |
| 6,669,557 B2 * | 12/2003 | Adams et al. ............... 460/7 |
| 6,839,616 B2 | 1/2005 | Beck |
| 6,848,243 B2 | 2/2005 | Carr et al. |
| 6,926,603 B2 * | 8/2005 | Kormann et al. ............... 460/1 |
| 7,398,636 B2 | 7/2008 | Carr et al. |
| 7,743,591 B2 | 6/2010 | Meier et al. |
| 7,861,606 B2 * | 1/2011 | Kormann ............... 73/863.53 |
| 2001/0054903 A1 * | 12/2001 | Adams et al. ............... 324/667 |
| 2002/0133309 A1 * | 9/2002 | Hardt ............... 702/129 |
| 2003/0063276 A1 | 4/2003 | Sjodin |
| 2003/0076118 A1 * | 4/2003 | Adams et al. ............... 324/664 |
| 2007/0186530 A1 * | 8/2007 | Meier et al. ............... 56/14.6 |
| 2009/0258684 A1 * | 10/2009 | Missotten et al. ............... 460/5 |
| 2010/0071333 A1 * | 3/2010 | Temple et al. ............... 56/14.6 |

* cited by examiner

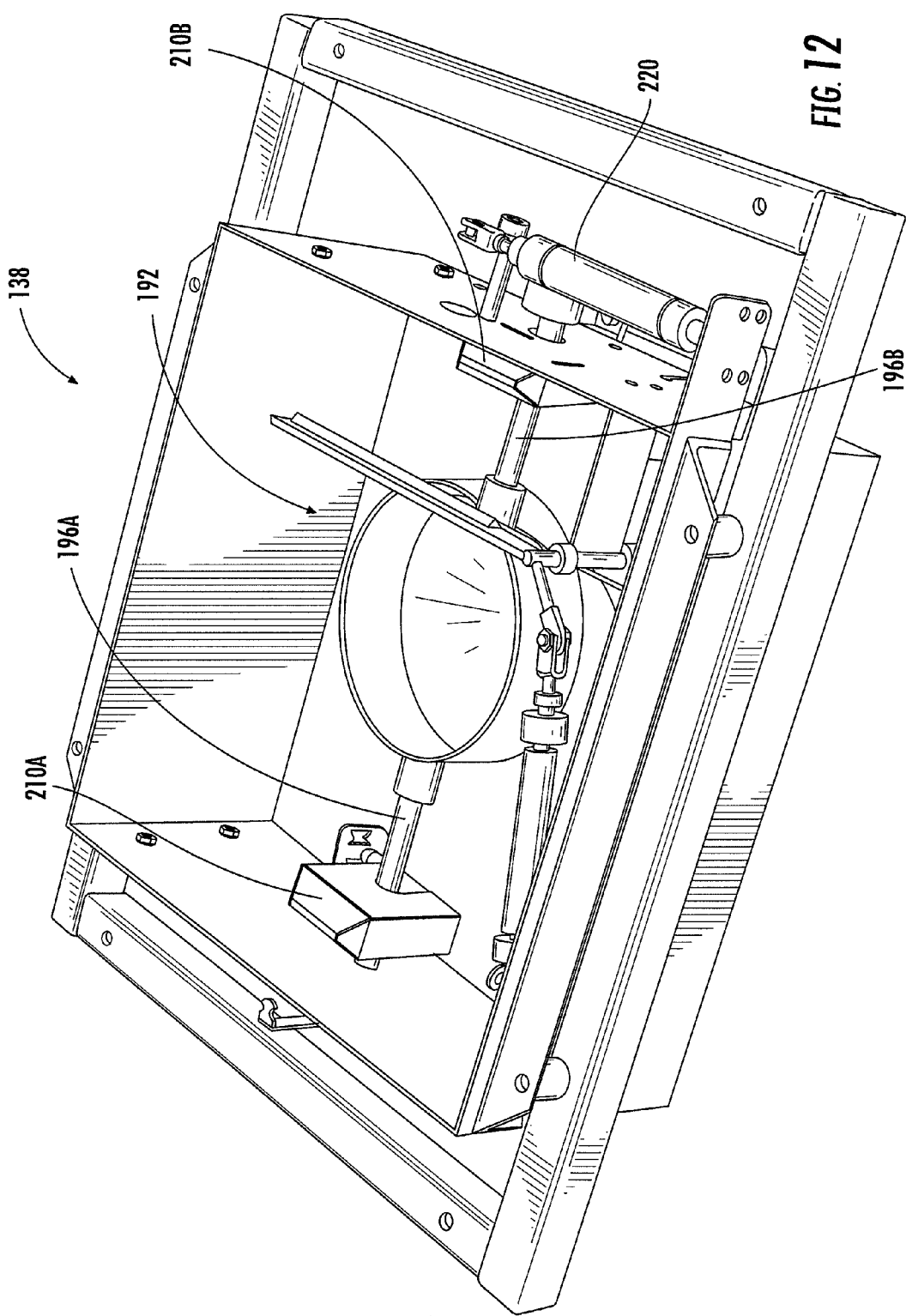

COMBINE HARVESTER AND ASSOCIATED METHOD FOR SELECTIVELY GATHERING GRAIN TEST DATA

CROSS-REFERENCE TO RELATED APPLICATIONS

The present application claims priority from U.S. Provisional Application No. 61/249,914 filed Oct. 8, 2009, which is hereby incorporated herein by reference in its entirety.

FIELD OF THE INVENTION

The various embodiments of the present invention relate generally to a combine harvester. More specifically, embodiments of the present invention relate to a combine harvester configured for gathering data.

BACKGROUND

A combine harvester (also known simply as a "combine") is a well-known machine used in agricultural applications. In general, combines are designed to travel through crop fields in order to harvest crop materials. Although combines may have various configurations, most are designed to separate grain from material-other-than-grain ("MOG"). Harvested grain is typically stored on board the combine and MOG is disposed back onto the crop field.

In general, a typical combine includes a crop harvesting apparatus (also referred to as a "header"), a threshing apparatus, and a grain delivery system. Although some headers may be used for various crops, a typical header is designed for use with a specific type of crop. As such, the header may be removable from the combine so that other headers configured for use with other crops may be attached in its place.

As the combine moves through a crop field, the header cuts the crops such that the resulting crop material (which at this point includes both grain and non-grain crop material) may be fed rearwardly into the threshing apparatus. Although there are various configurations of threshing apparatuses, a typical axial-flow threshing apparatus includes a threshing rotor which is mounted axially within the combine and which is substantially surrounded by a rotor housing comprising an arrangement of relatively small openings. As the crop material travels rearwardly through the threshing apparatus, the threshing rotor threshes the crop material against the inside surface of the rotor housing. This action separates grain from the MOG.

The MOG typically continues to move through the rotor housing due to the rotation of the rotor and is ultimately released out of the tail end of the rotor and is disposed onto the crop field, in some cases aided by a supplemental spreading device. The smaller grain falls through the openings of the rotor housing and onto a series of sieves that move back and forth. The sieves include an arrangement of smaller openings that further separate the heavier grain from any other non-grain crop material.

Once the grain falls through the moving sieves, it reaches a grain pan. A clean grain auger may be proximate the bottom of the pan. The clean grain auger moves the grain transversely to one side of the combine, where it travels to the grain hopper via a clean grain elevator. Typically, the moving sieves, clean grain auger, and clean grain elevator are mechanically actuated via a belt and pulley system driven by the combine engine so as to associate the speed of the sieves, auger, and grain elevator with the speed of the combine engine.

In a typical harvesting application, the combine is configured to send all of the harvested grain directly to the grain hopper. In some instances, however, it would be desirable to test and/or sample at least a portion of the harvested grain for various characteristics. Such instances could arise, for example, in research applications where crop fields may include experimental crops or other crops for which gathering test data may be advantageous. In addition, commercial harvesting applications could also benefit from an ability to test and/or sample at least a portion of the harvested grain.

As a result, there is a need in the art for a combine harvester and method configured for gathering grain test data. In addition, there is a need in the art for a combine harvester and method configured to sample at least a portion of the tested grain. In various embodiments, the combine harvester and method should provide the ability to selectively test and/or sample the grain without substantially affecting normal operation of the combine.

SUMMARY OF VARIOUS EMBODIMENTS

The present invention addresses the above needs and achieves other advantages by providing a combine harvester and associated method for gathering grain test data. In general, the combine harvester comprises a threshing assembly configured to separate grain from other crop material, a grain delivery assembly comprising a clean grain auger and a clean grain elevator, the grain delivery assembly configured to receive grain from the threshing assembly and deliver the grain along a harvesting path to a primary grain hopper, and a grain diverting assembly located proximate an interface between the clean grain auger and the clean grain elevator. The grain diverting assembly is configured to selectively divert grain from the harvesting path to a grain testing path where at least a portion of the diverted grain is delivered to a test stage configured to gather grain test data. In some embodiments, the clean grain auger may receive the grain from the threshing assembly and the clean grain elevator may deliver the grain to the primary grain hopper.

In some embodiments, the grain diverting assembly may comprise a transfer tube through which grain is transported from the threshing assembly by the clean grain auger, the transfer tube including a cutout located on a bottom portion thereof, a gate located between the transfer tube and the clean grain elevator configured to be positioned in a harvest position and a diverted position, and a rotating sleeve configured to rotate about an outer periphery of the transfer tube, the rotating sleeve also including a cutout portion configured to be positioned in a harvest position and a diverted position, wherein in the harvest position, the gate is open and the transfer tube cutout and the sleeve cutout are not aligned so that grain transported from the threshing assembly is delivered to the clean grain elevator, and wherein in the diverted position the gate is closed and the transfer tube cutout and the sleeve cutout are substantially aligned so that grain transported from threshing assembly is delivered to the test stage.

Some embodiments may further comprise a test delivery system configured to deliver the diverted grain to the test stage. In some embodiments, the test delivery system may utilize vacuum pressure to deliver the diverted grain to the test stage. In some embodiments, the test delivery system may include a test grain cyclone and a dust collection cyclone. In some embodiments, the test stage may comprise at least one of a moisture test station, a bulk density station, and a plot weight station. In some embodiments, the test stage may comprise at least a bulk density station and the bulk density station may include a bulk density cup supported by at least one load measuring device. In some embodiments, the bulk density station may further include a scraper device configured to sweep across a top plane of the bulk density cup to remove any excess amount of diverted grain and to ensure that the bulk density cup includes a predetermined volume of grain therein.

In some embodiments, the bulk density station may further include at least one calibration weight configured to load the bulk density cup with a known load, and the combine harvester may further comprise a control device configured to automatically load the bulk density cup with the calibration weight to calibrate the load measuring device. In some embodiments, the bulk density station may include a rotatable bulk density cup comprising a cup body and first and second cup axles extending opposite each other from the cup body, and the first and second cup axles may be supported by respective first and second load measuring devices. In some embodiments, the bulk density station may further include respective first and second calibration weights configured to load the first and second cup axles with a known load, and the combine harvester may further comprise a control device configured to automatically load the first and second cup axles with the first and second calibration weights to calibrate the first and second load measuring devices. In some embodiments, the test stage may comprise at least a plot weight station and the plot weight station may include a plot weight hopper supported by at least one load measuring device. In some embodiments, the plot weight station may further include at least one calibration weight configured to load the plot weight hopper with a known load, and the combine harvester may further comprise a control device configured to automatically load the plot weight hopper with the calibration weight to calibrate the load measuring device.

Some embodiments may further comprise a combine operator location, a sampling cup located within the grain testing path, the sampling cup configured to receive a sample portion of the diverted grain, and a sample delivery system configured to deliver the sample portion of diverted grain to the combine operator location. In some embodiments, the sample delivery system may utilize vacuum pressure to deliver the sample portion of the diverted grain to the combine operator location. In some embodiments, the sample delivery system may include a sample cyclone.

Another embodiment of the present invention provides a method for selectively gathering grain test data using a combine harvester having a threshing assembly, a primary grain hopper, and a grain delivery assembly comprising a clean grain auger and a clean grain elevator. In general, the method comprises separating grain from other crop material using the threshing assembly, receiving grain from the threshing assembly and delivering the grain along a harvesting path to the primary grain hopper using the grain delivery system, selectively diverting grain from the harvesting path to a grain testing path using a diverting assembly located proximate an interface between the clean grain auger and the clean grain elevator, delivering at least a portion of the diverted grain to a test stage of the combine harvester, and gathering grain test data using the test stage. In some embodiments, receiving grain from the threshing assembly and delivering the grain along a harvesting path to the primary grain hopper may comprise receiving the grain from the threshing assembly with the clean grain auger and delivering the grain to the primary grain hopper with the clean grain elevator.

Some embodiments may further comprise transporting grain from the threshing assembly through a transfer tube using the clean grain auger, the transfer tube including a cutout located on a bottom portion thereof, and positioning a gate located between the transfer tube and the clean grain elevator in a harvest position and a diverted position and positioning a cutout of a rotating sleeve in a harvest position and a diverted position, wherein in the harvest position, the gate is positioned open and the rotating sleeve is positioned so that the rotating sleeve cutout is not aligned with the transfer tube cutout and grain is transported from the threshing assembly to the clean grain elevator, and wherein in the diverted position the gate is positioned closed and the rotating sleeve is positioned so that the rotating sleeve cutout is substantially aligned with the transfer tube cutout and grain is transported from threshing assembly to the test stage.

Some embodiments may further comprise delivering the diverted grain to the test stage using a test delivery system. In some embodiments, the test delivery system may utilize vacuum pressure to deliver the diverted grain to the test stage. In some embodiments, the test delivery system may include a test grain cyclone and a dust collection cyclone. In some embodiments, the test stage may comprise at least one of a moisture test station, a bulk density station, and a plot weight station. In some embodiments, the test stage may comprise at least a bulk density station and the bulk density station may include a bulk density cup supported by at least one load measuring device. Some embodiments may further comprise sweeping a scraper device across a top plane of the bulk density cup to remove any excess amount of diverted grain and to ensure that the bulk density cup includes a predetermined volume of grain therein.

Some embodiments may further comprise using a control device to automatically load the bulk density cup with at least one calibration weight of a known load, and calibrating the load measuring device with the control device. In some embodiments, the bulk density station may include a rotatable bulk density cup comprising a cup body and first and second cup axles extending opposite each other from the cup body, and the first and second cup axles may be supported by respective first and second load measuring devices. Some embodiments further comprise using a control device to automatically load the first and second axles of the bulk density cup with respective first and second calibration weights of known loads, and calibrating the first and second load measuring devices with the control device. In some embodiments, the test stage may comprise at least a plot weight station and the plot weight station may include a plot weight hopper supported by at least one load measuring device. Some embodiments may further comprise using a control device to automatically load the plot weight hopper with at least one calibration weight of a known load, and calibrating the load measuring device with the control device.

Some embodiments may further comprise receiving a sample portion of the diverted grain in a sampling cup located within the grain testing path, and delivering the sample portion of diverted grain to a combine operator location of the combine harvester. In some embodiments, the sample delivery system may utilize vacuum pressure to deliver the sample portion of the diverted grain to the combine operator location. In some embodiments, the sample delivery system may include a sample cyclone.

BRIEF DESCRIPTION OF THE DRAWINGS

Figure 1:
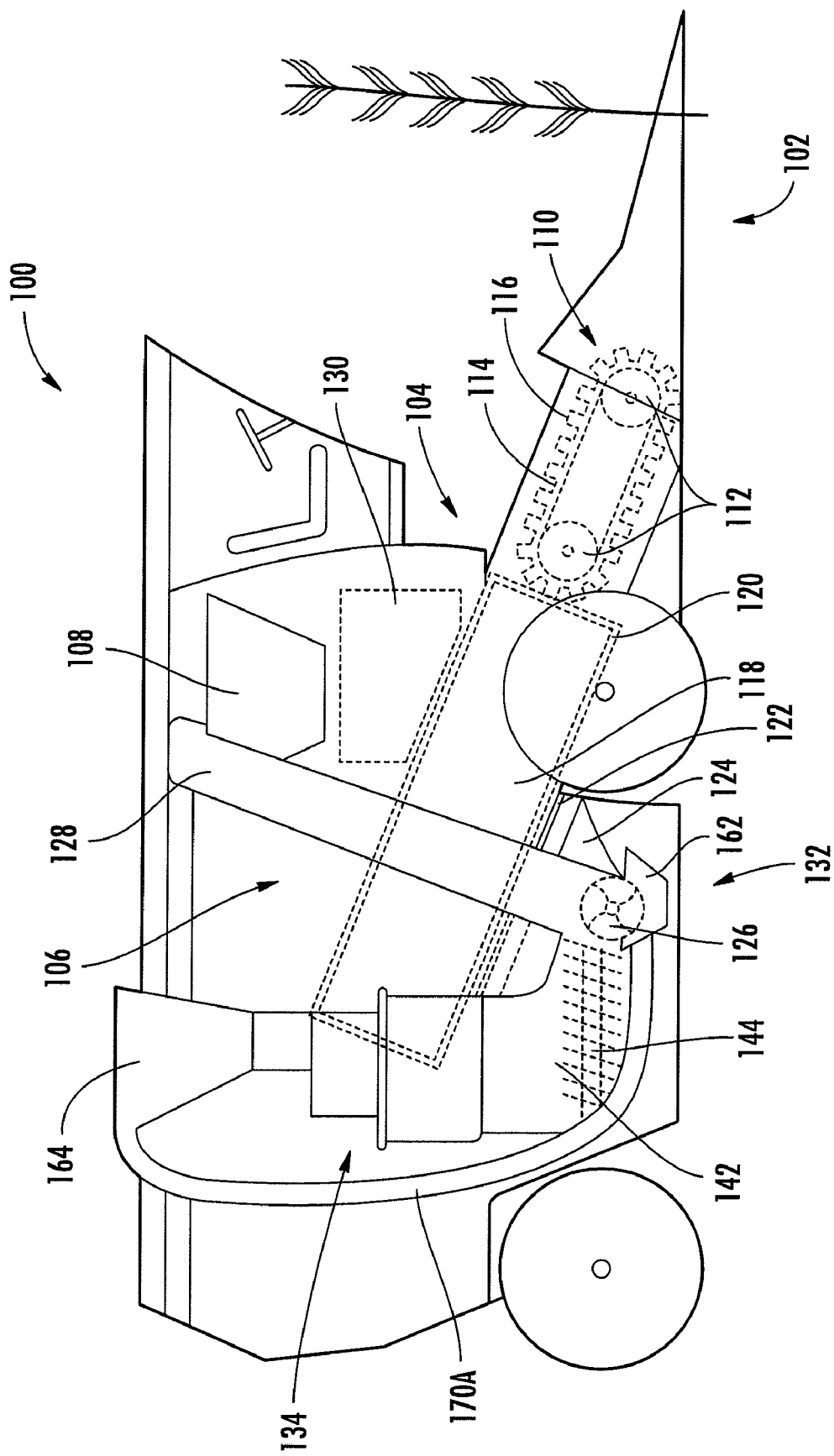
Figure 2:
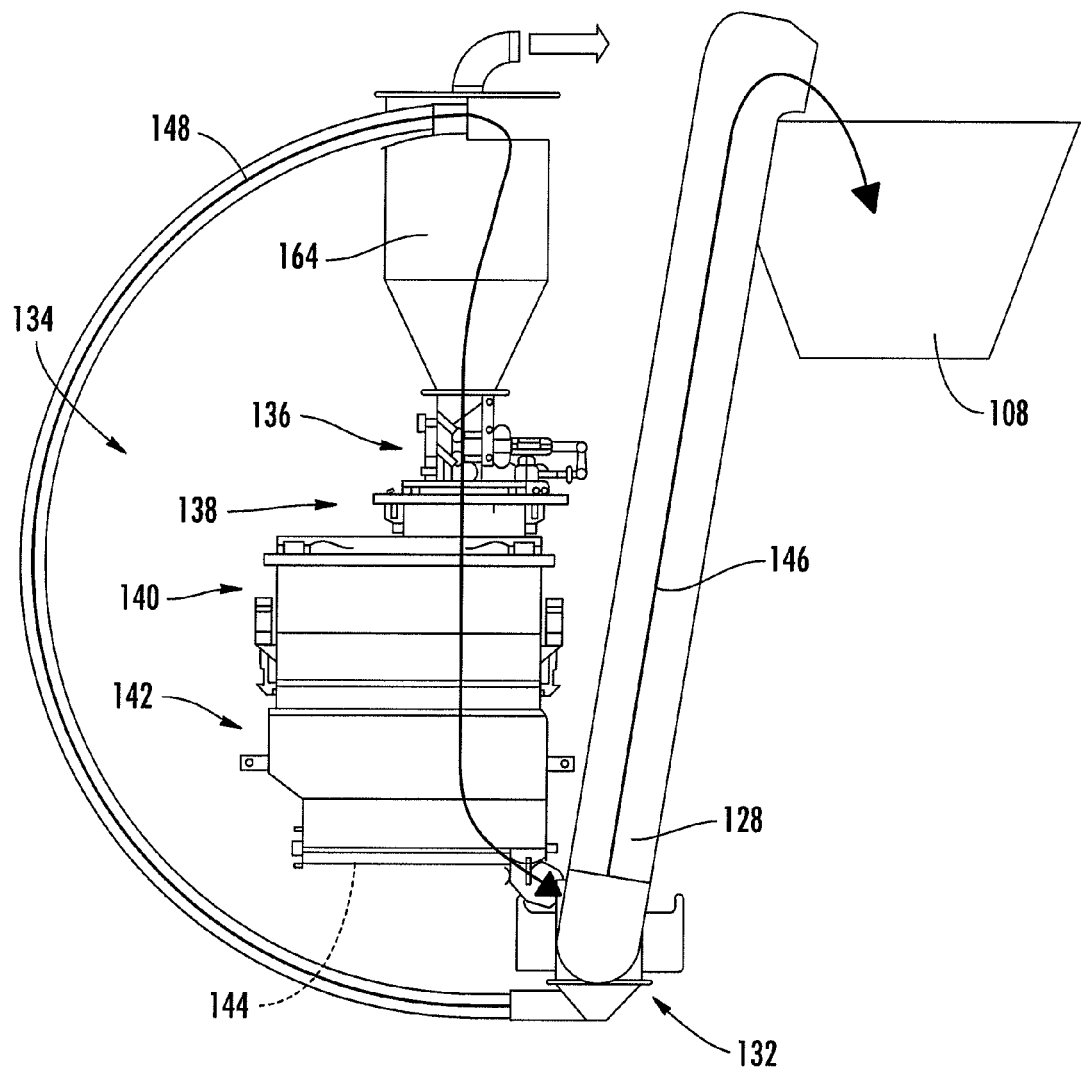
Figure 3:
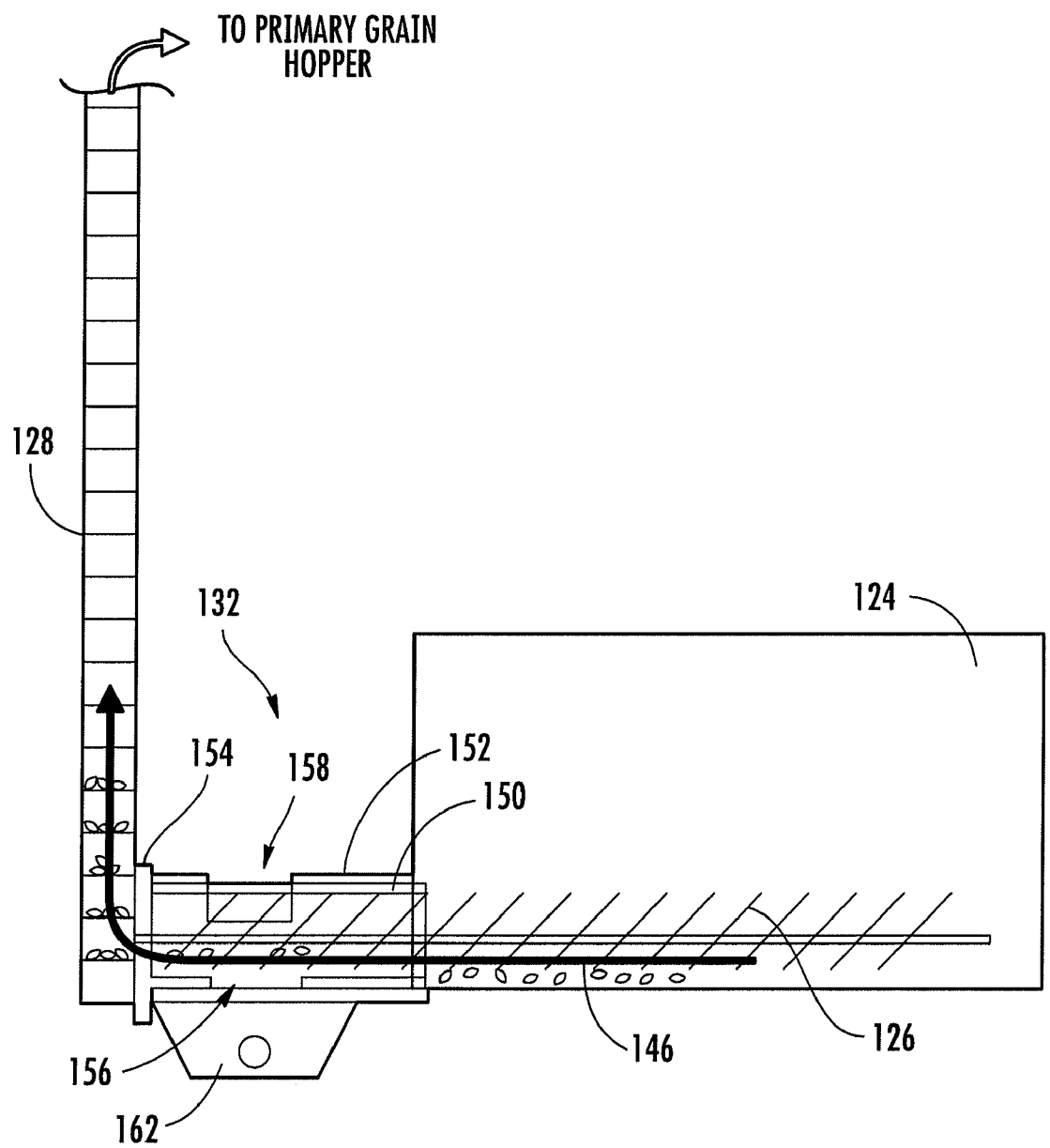
Figure 4:
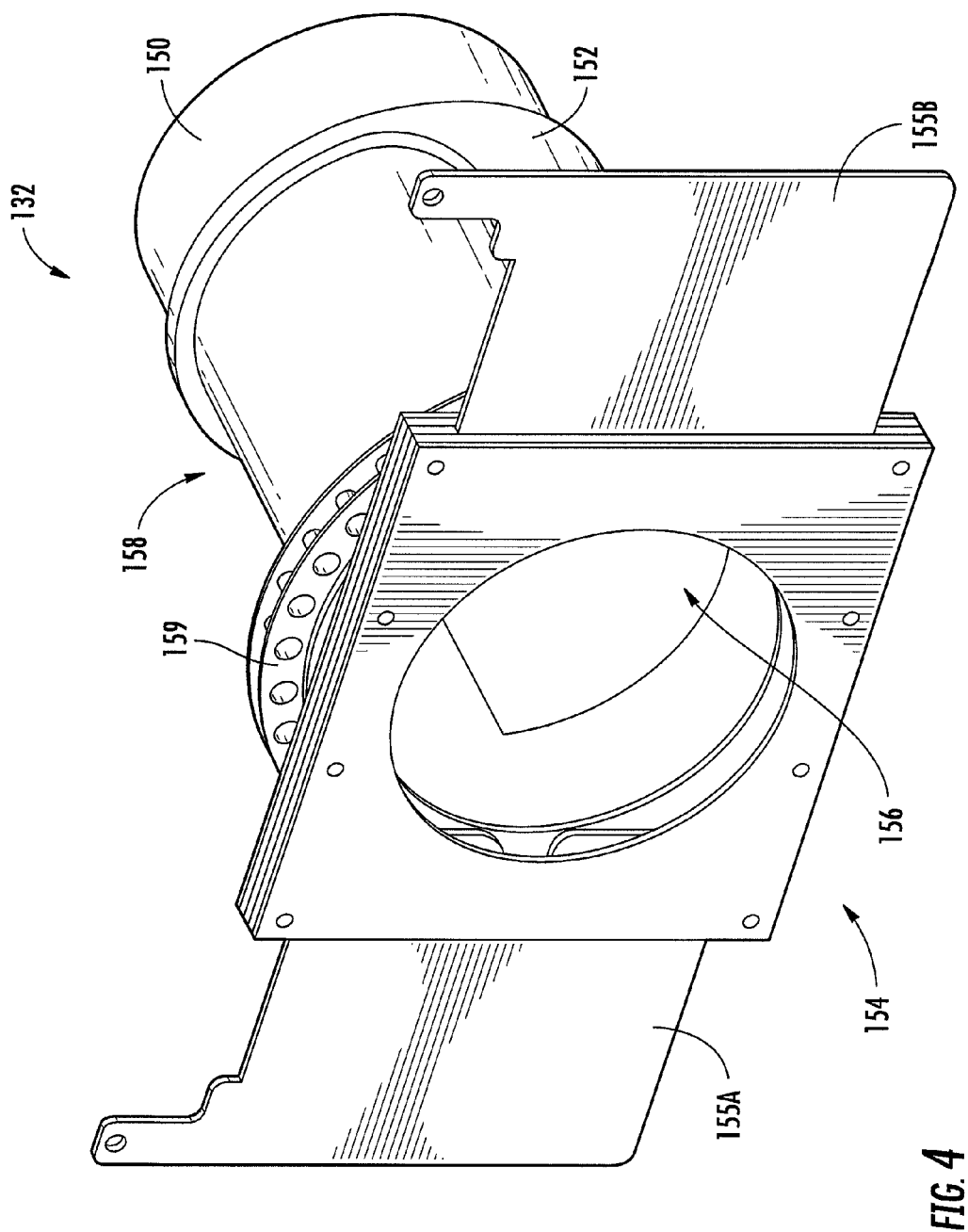
Figure 4A:
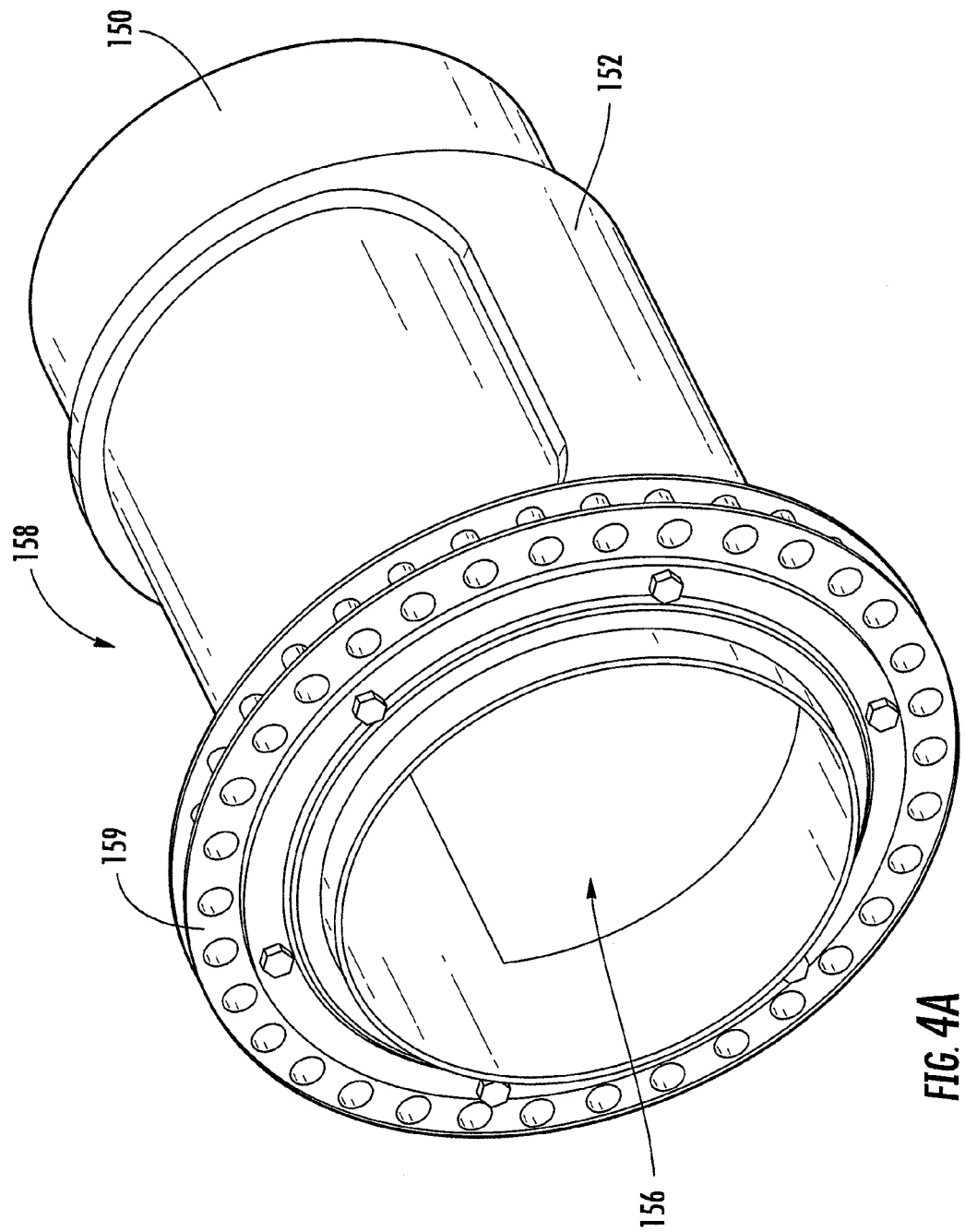
Figure 5:
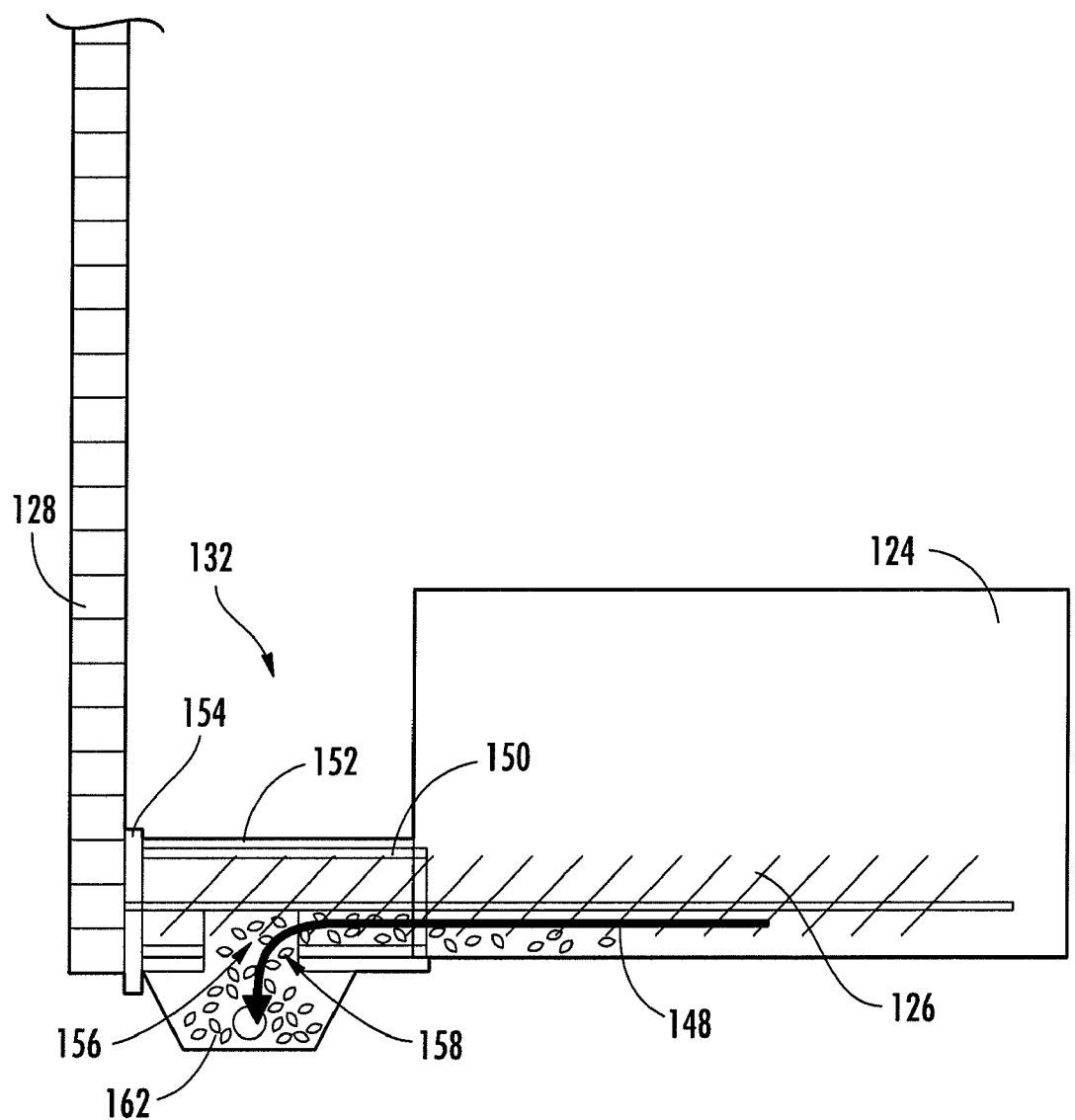
Figure 6:
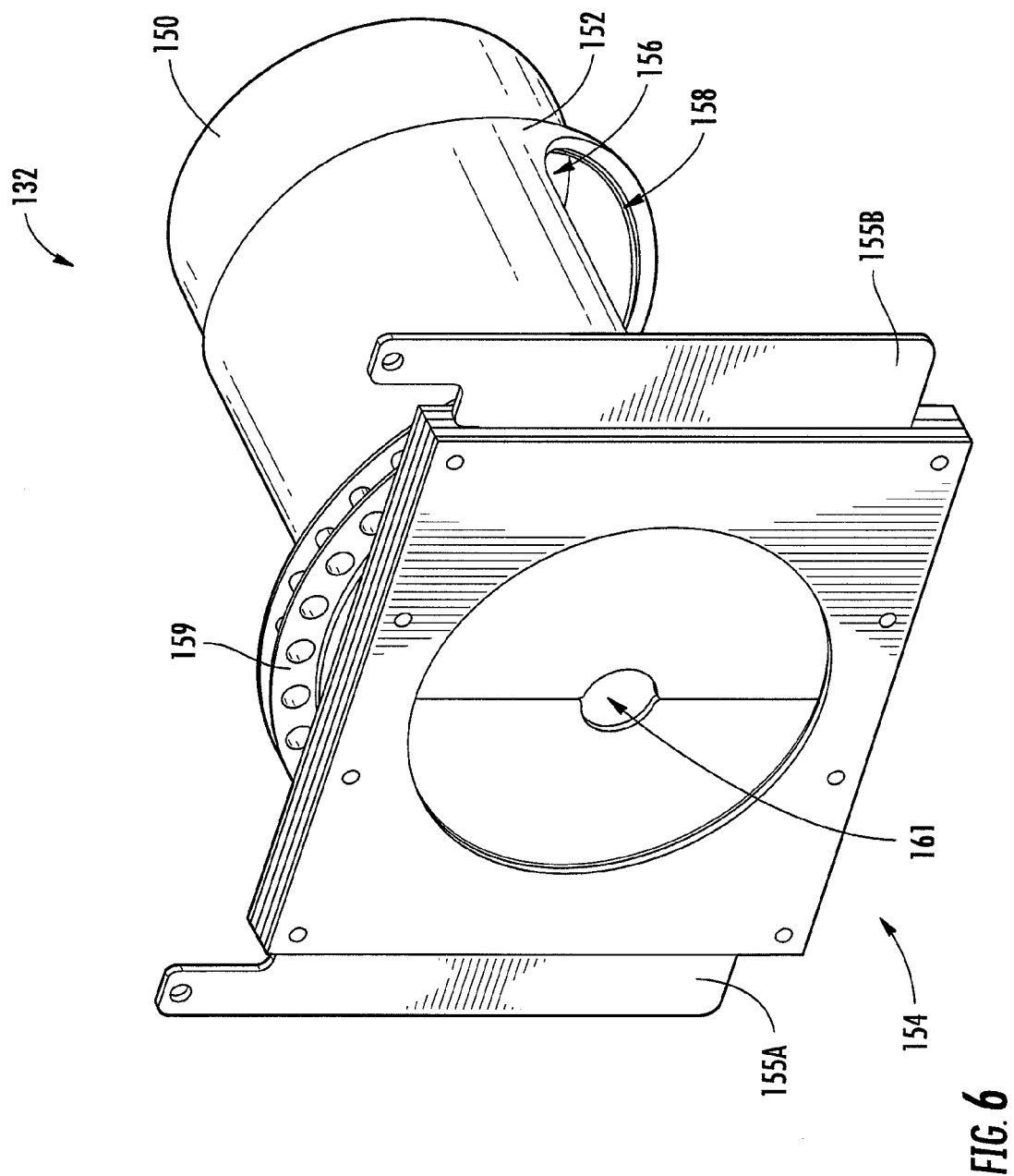
Figure 6A:
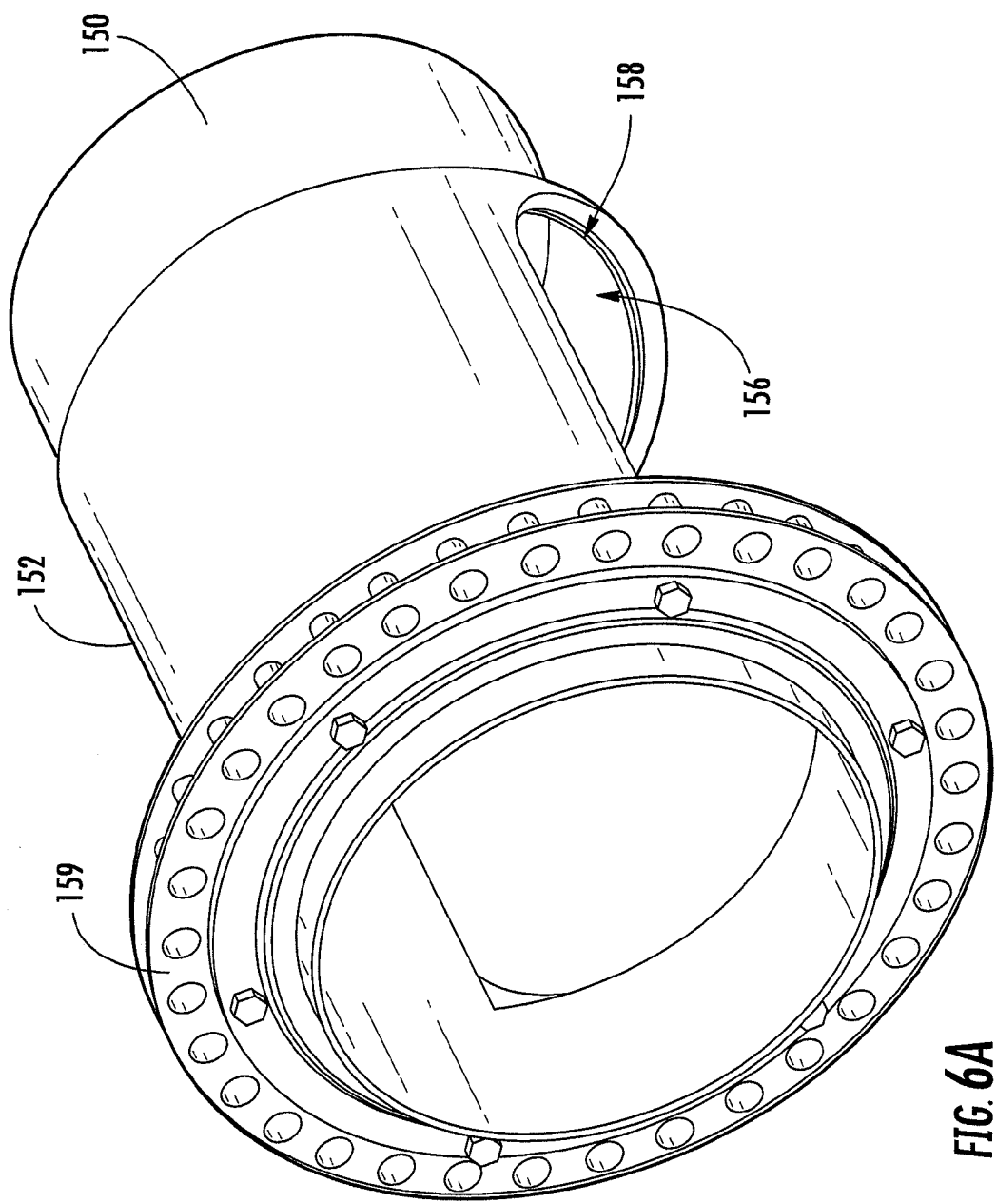
Figure 7:
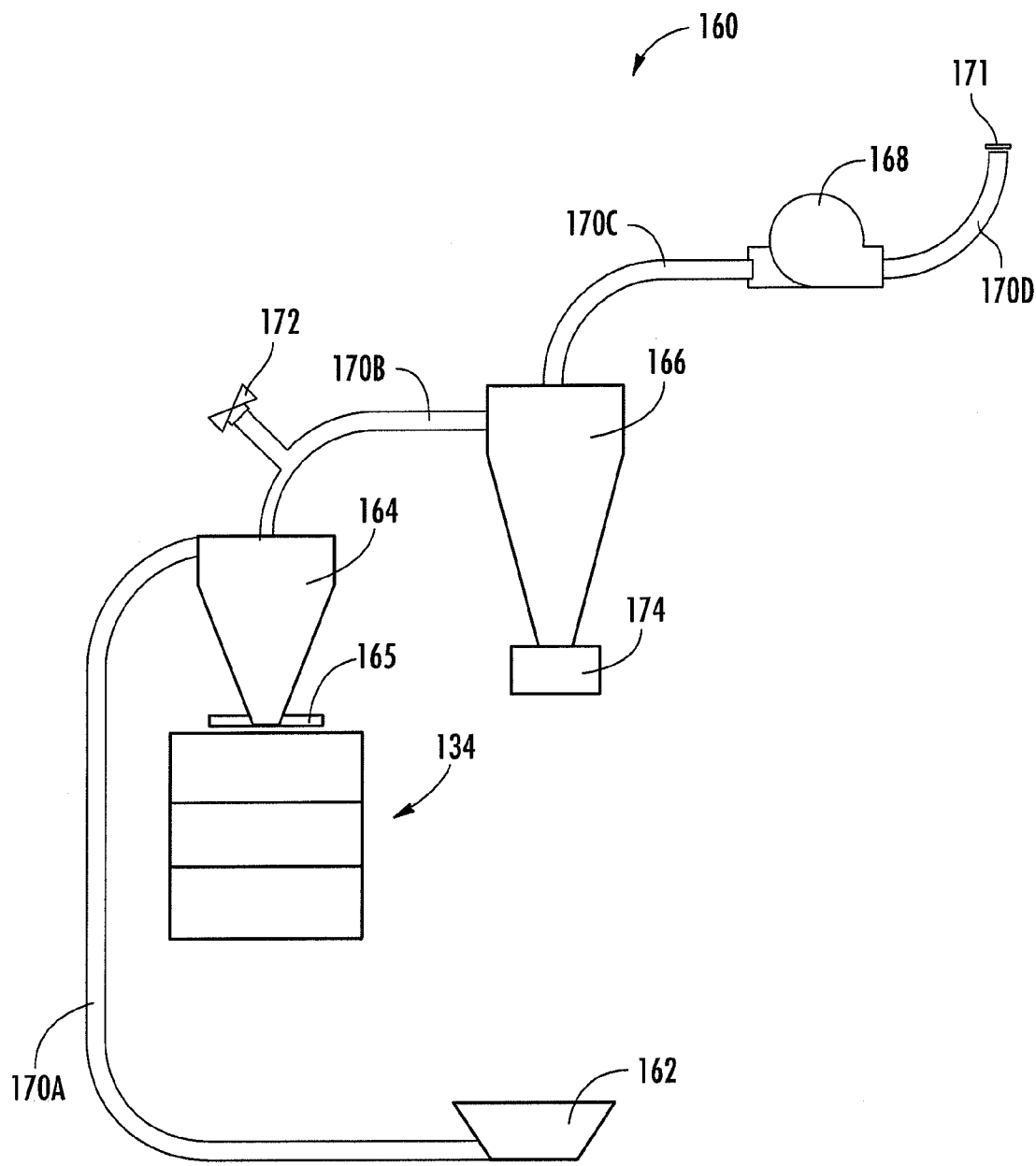

Having thus described the invention in general terms, reference will now be made to the accompanying drawings, which are not necessarily drawn to scale, and wherein:

FIG. 1 depicts a side schematic view of a combine harvester in accordance with an exemplary embodiment of the present invention;

FIG. 2 depicts a side schematic view of various components of the combine harvester showing a portion of a harvesting path and a grain testing path in accordance with an exemplary embodiment of the present invention;

FIG. 3 depicts a front section view of a grain diverting assembly shown in a harvest position in accordance with an exemplary embodiment of the present invention;

FIG. 4 depicts a perspective view of a grain diverting assembly shown in a harvest position in accordance with an exemplary embodiment of the present invention;

FIG. 4A depicts a perspective view of the transfer tube and rotating sleeve of the grain diverting assembly of FIG. 4, shown in the harvest position;

FIG. 5 depicts a front section view of a grain diverting assembly shown in a diverted position in accordance with an exemplary embodiment of the present invention;

FIG. 6 depicts a perspective view of a grain diverting assembly shown in a diverted position in accordance with an exemplary embodiment of the present invention;

FIG. 6A depicts a perspective view of the transfer tube and rotating sleeve of the grain diverting assembly of FIG. 6, shown in the diverted position;

FIG. 7 depicts a schematic view of a test delivery system configured to operate under vacuum pressure in accordance with an exemplary embodiment of the present invention.

Figure 8:
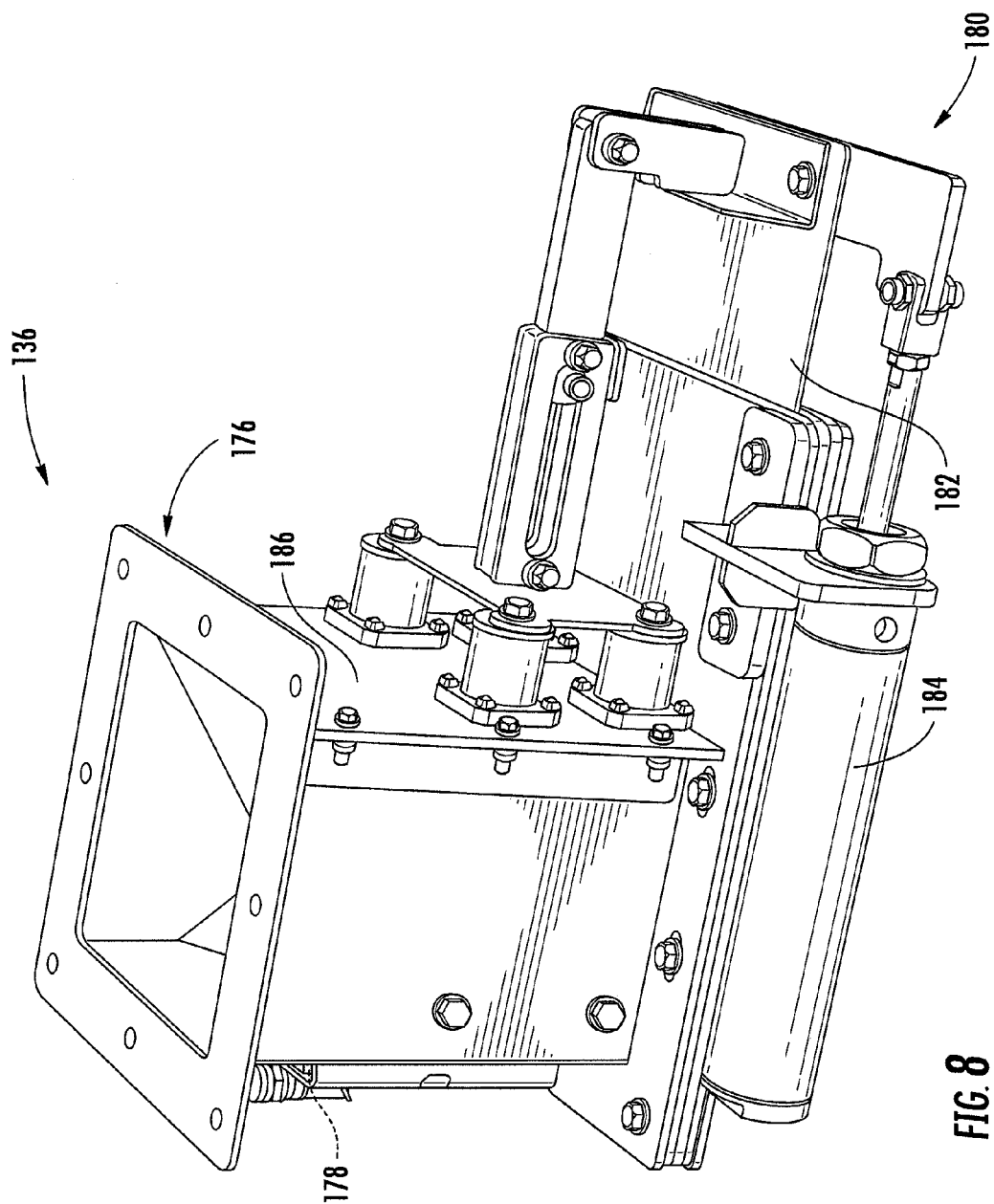
Figure 8A:
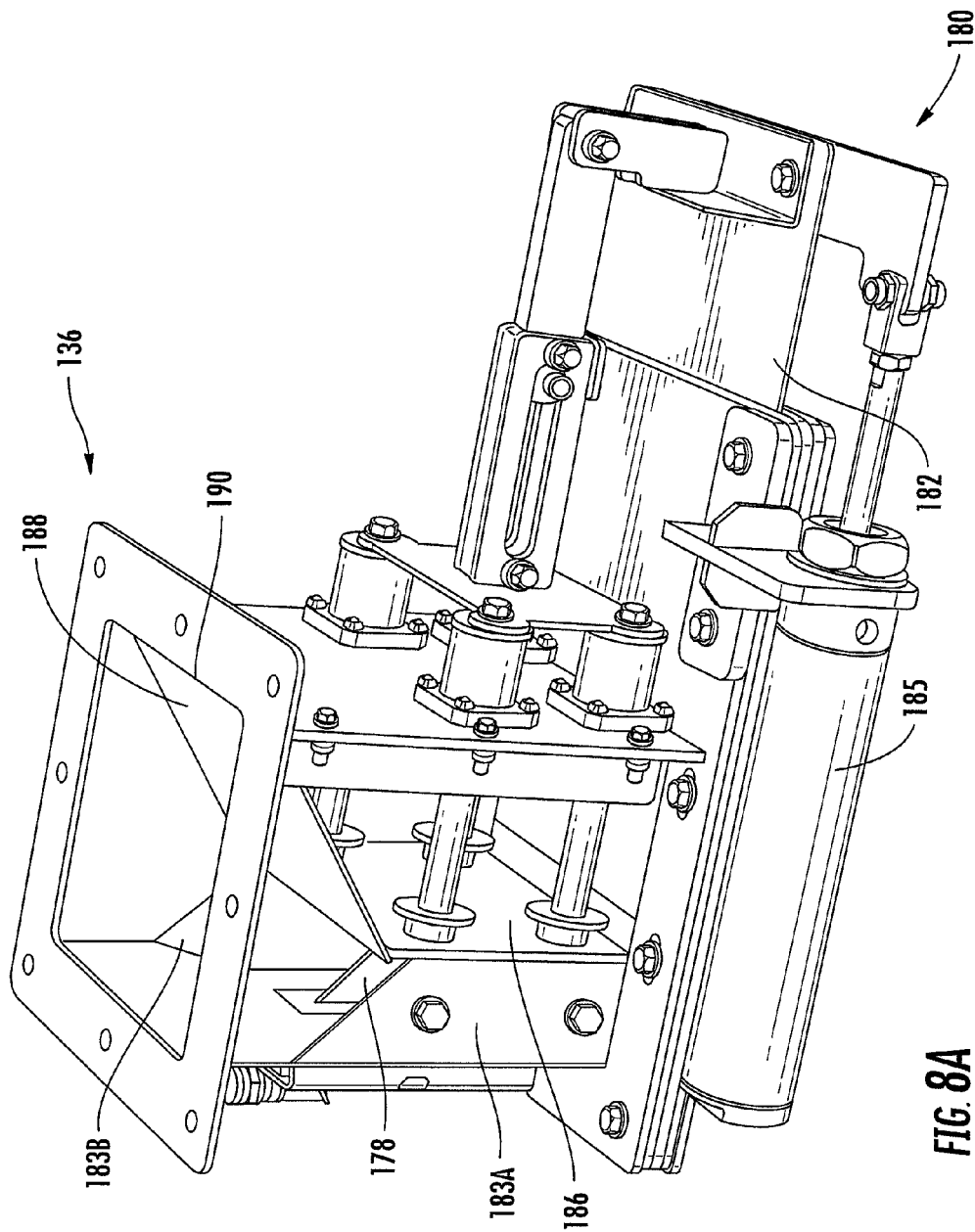
Figure 9:
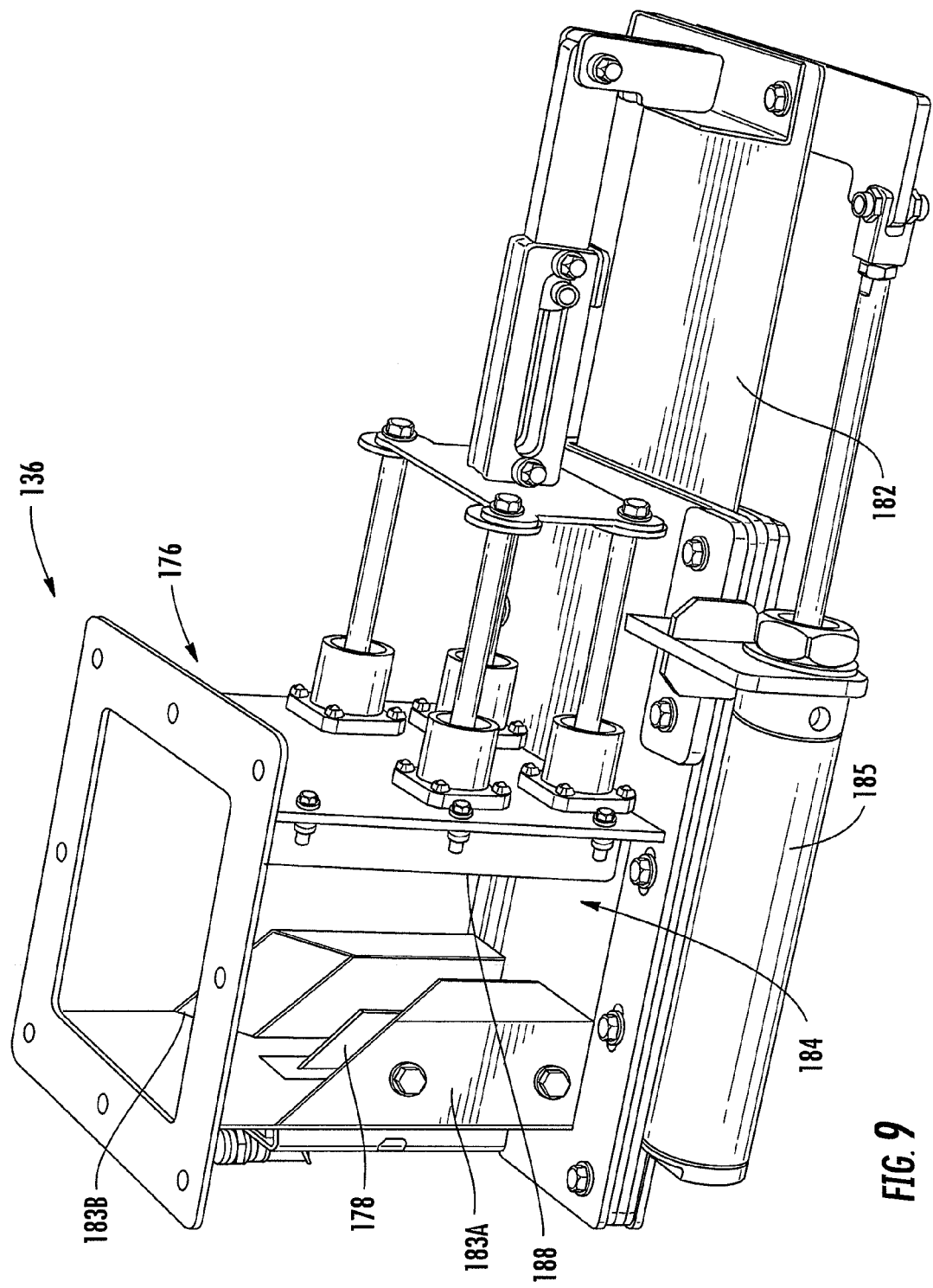
Figure 10:
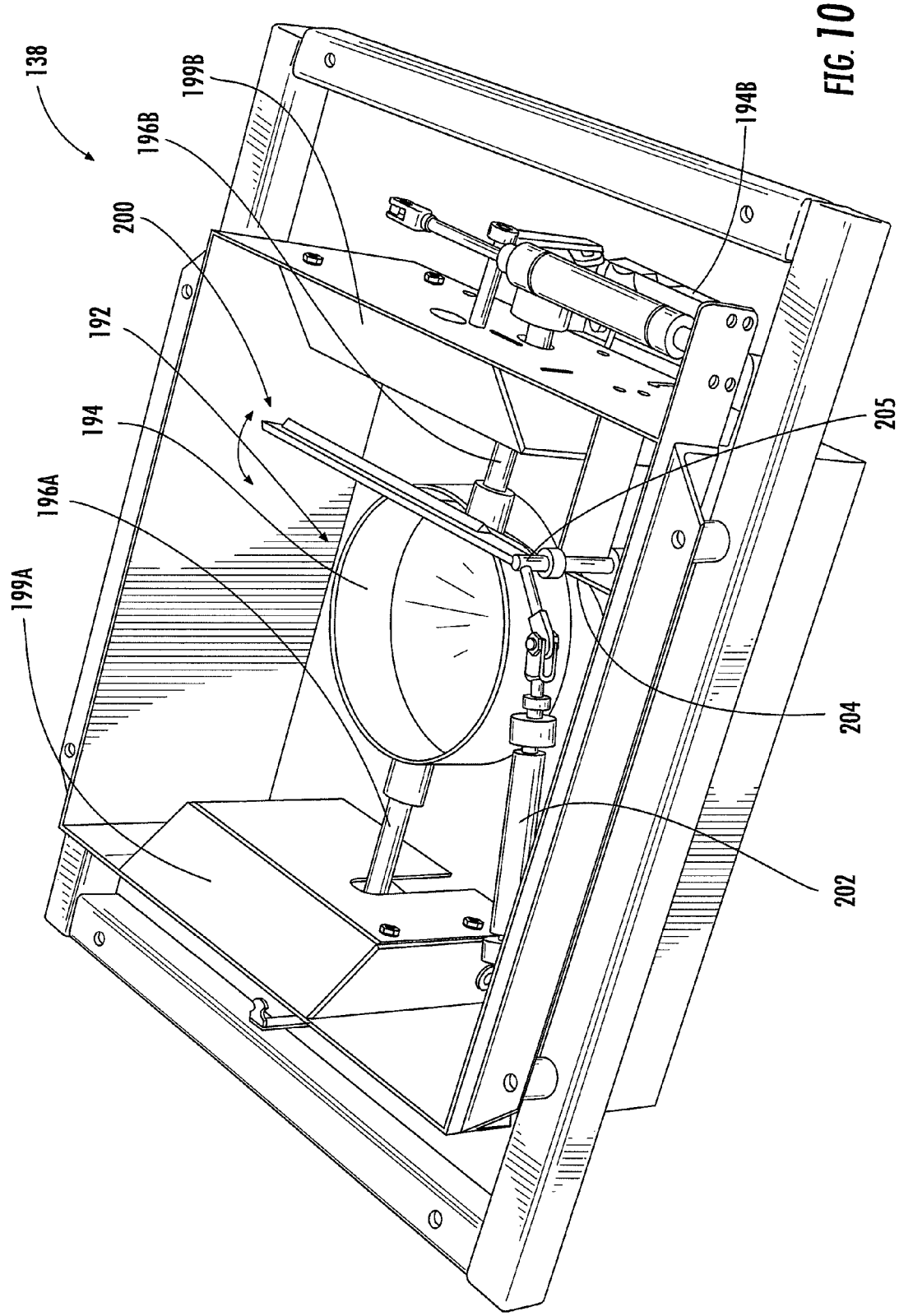
Figure 11:
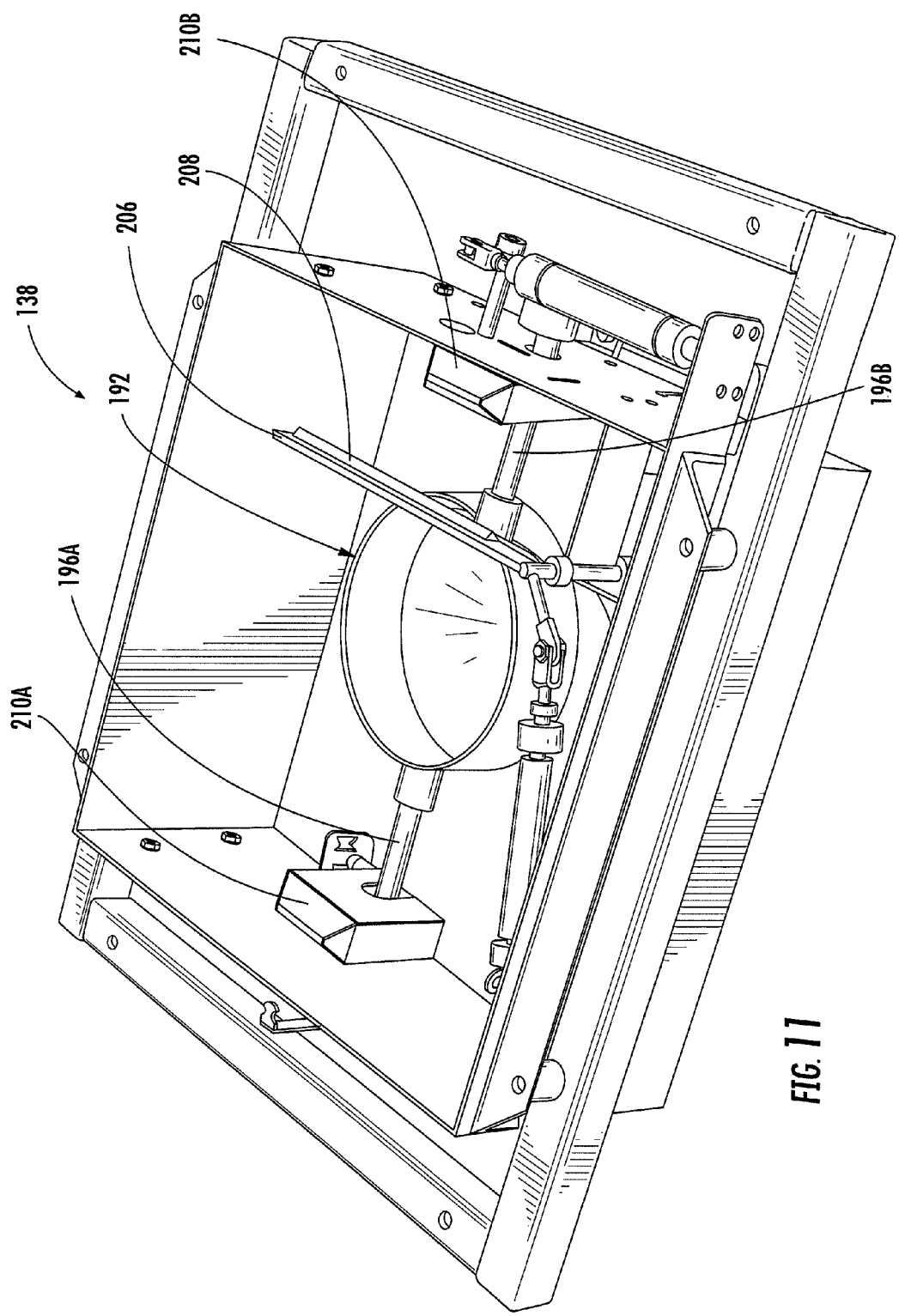
Figure 11A:
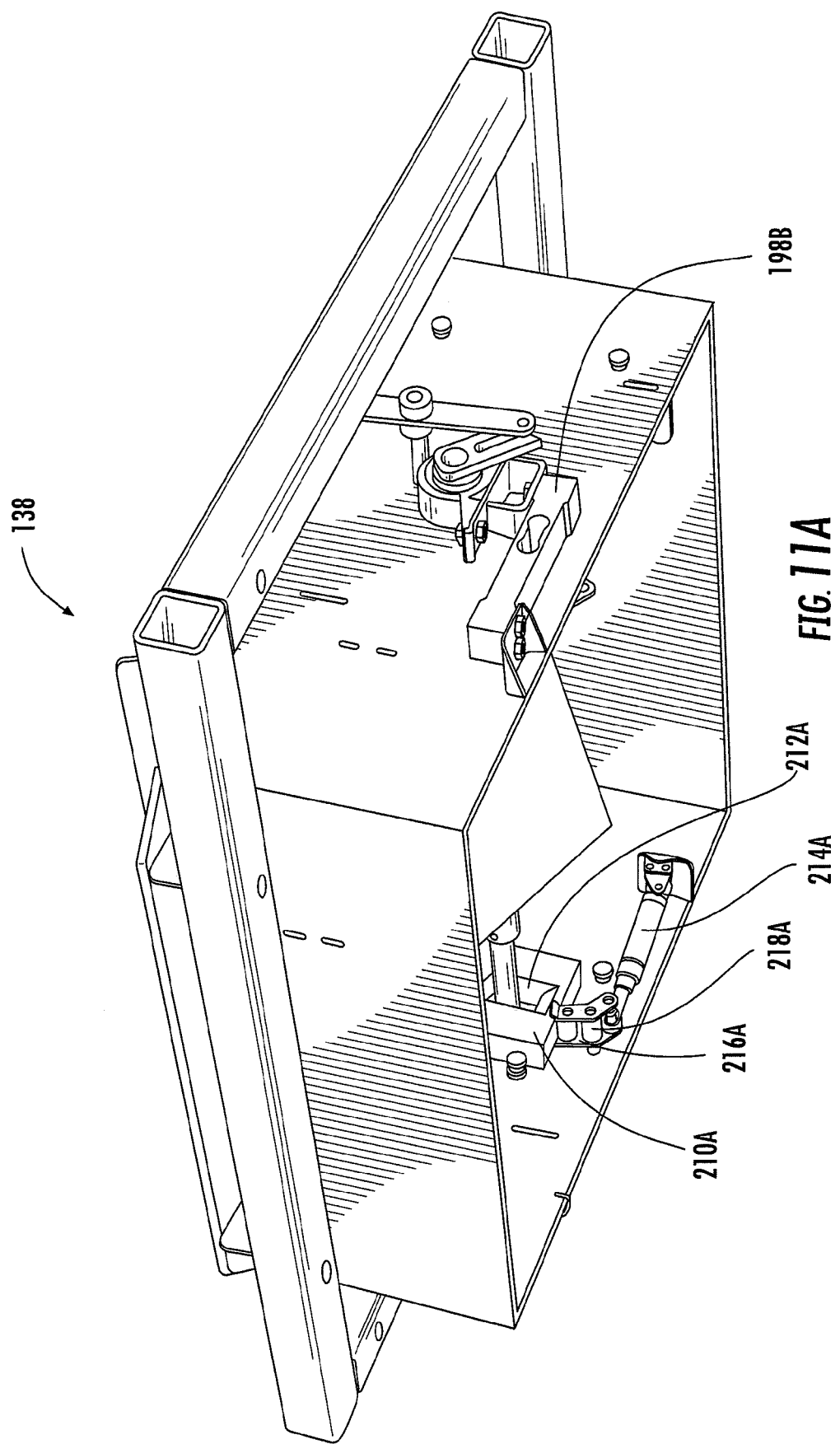
Figure 12A:
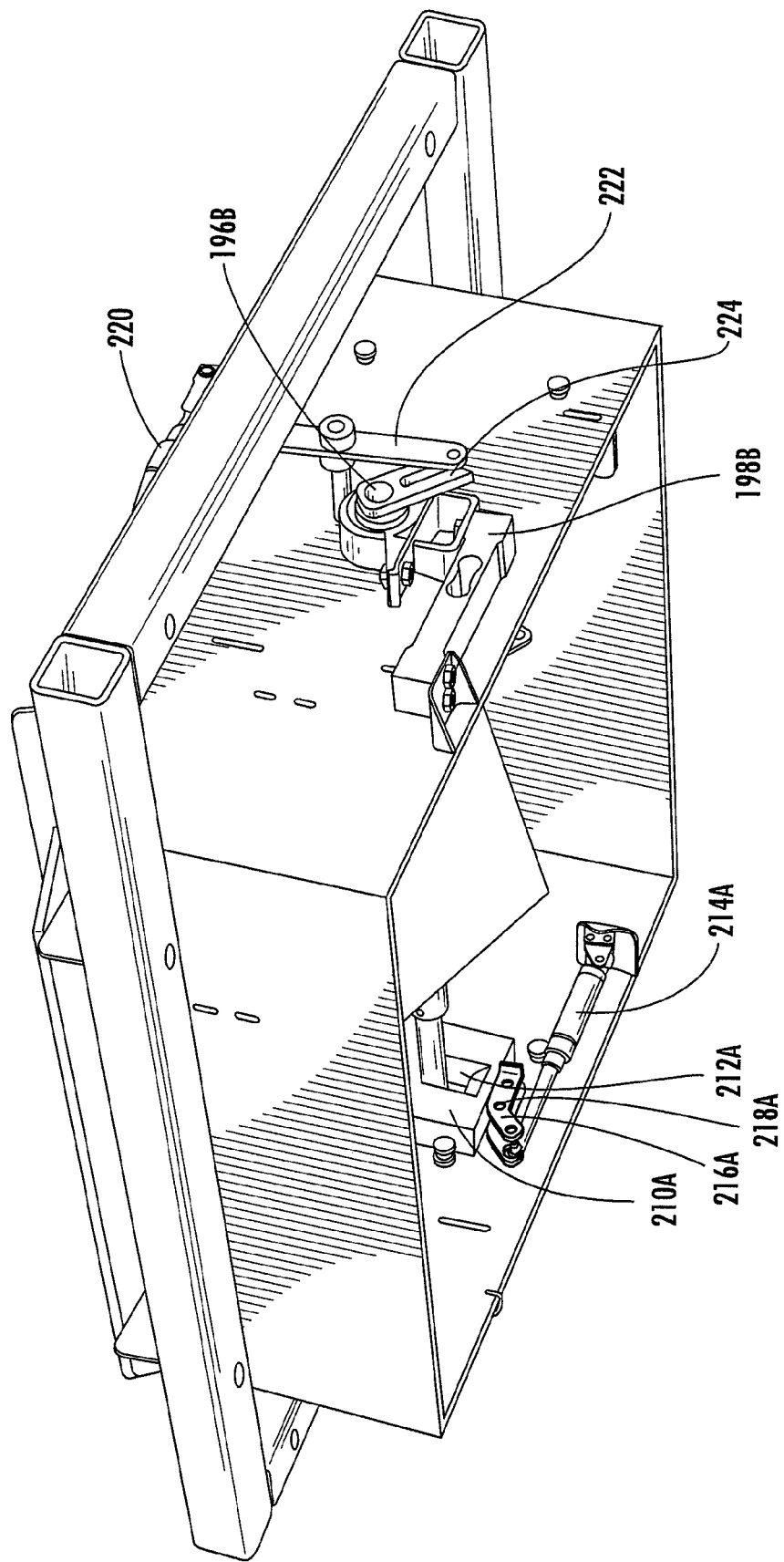
Figure 13:
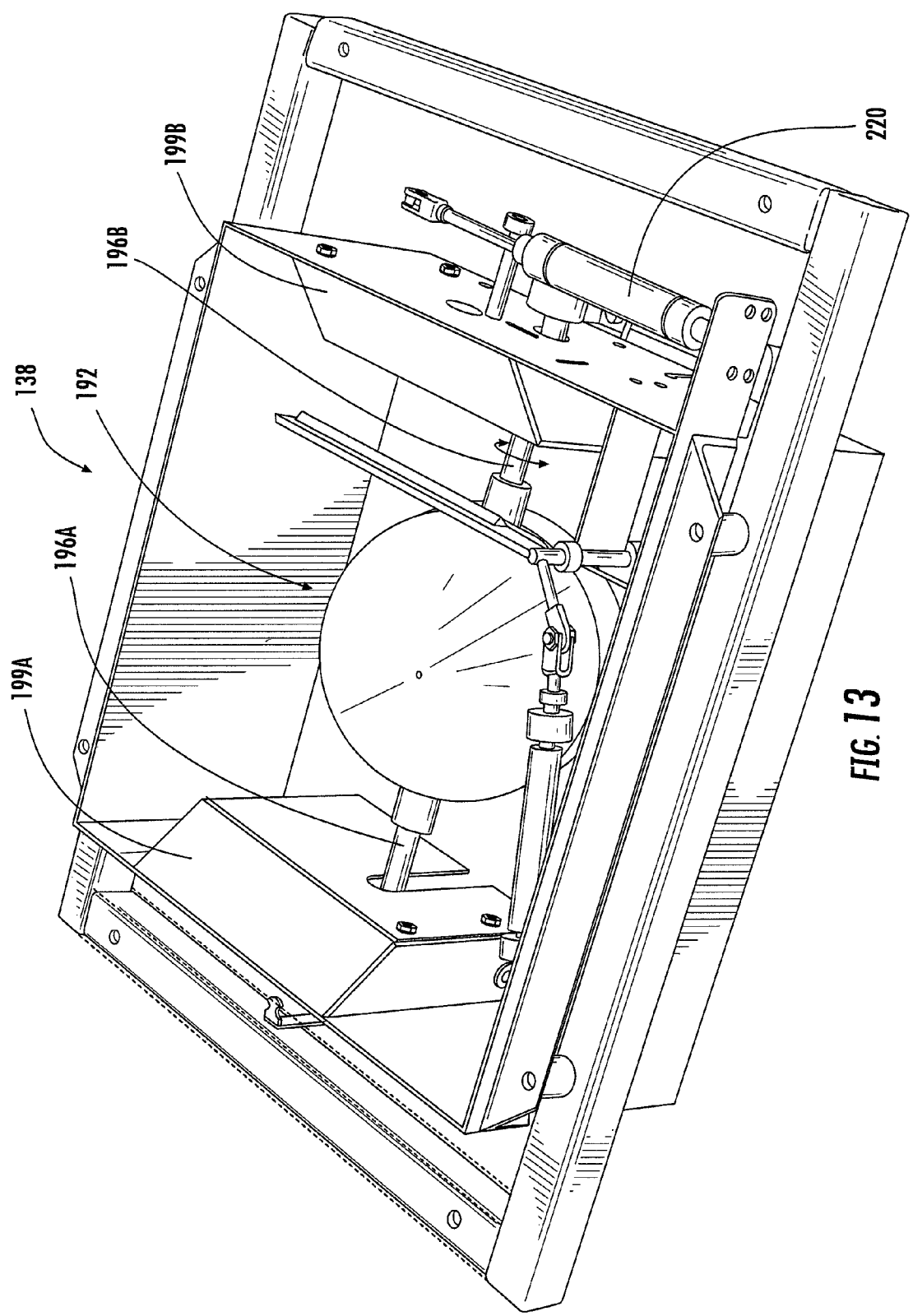
Figure 14:
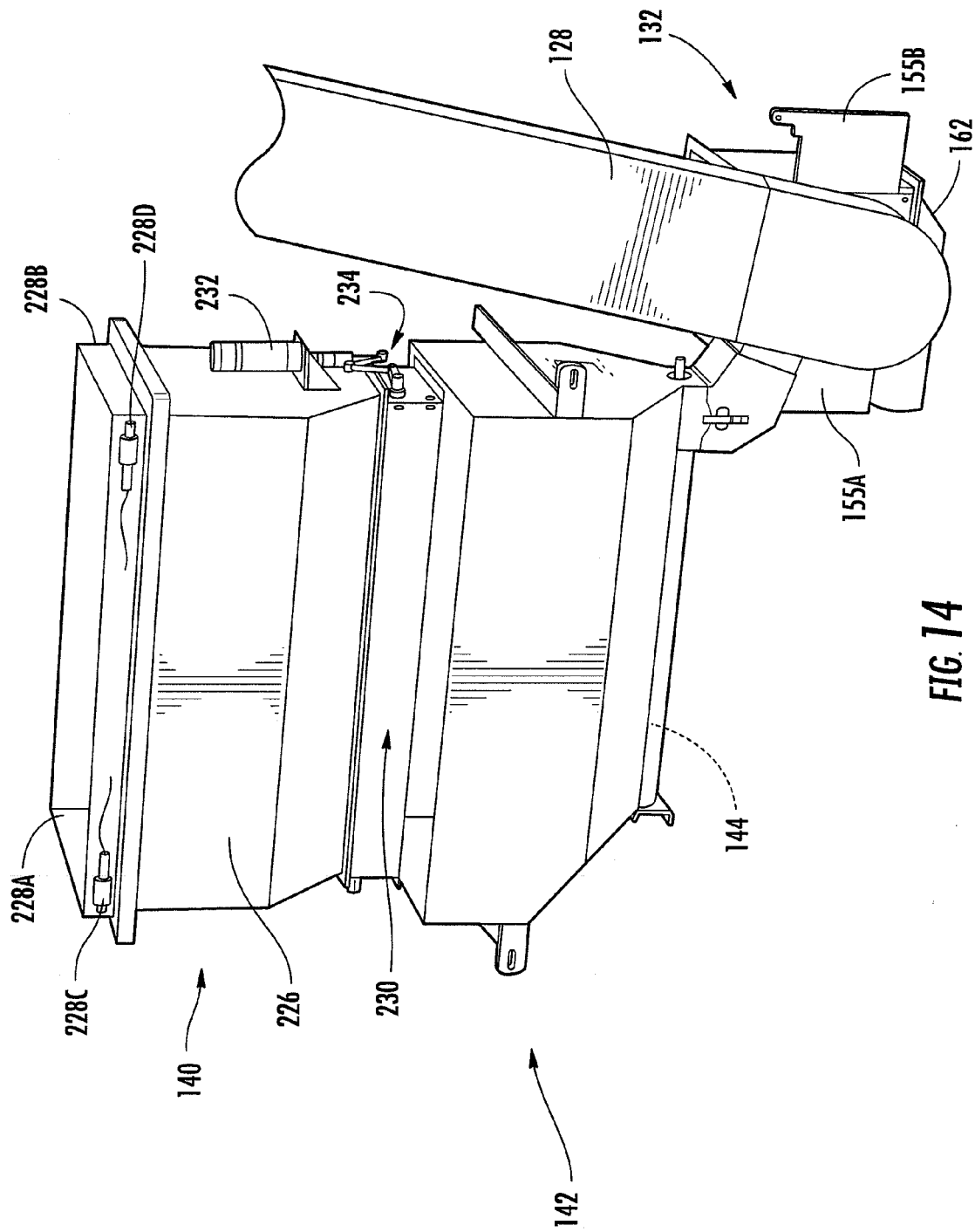
Figure 15:
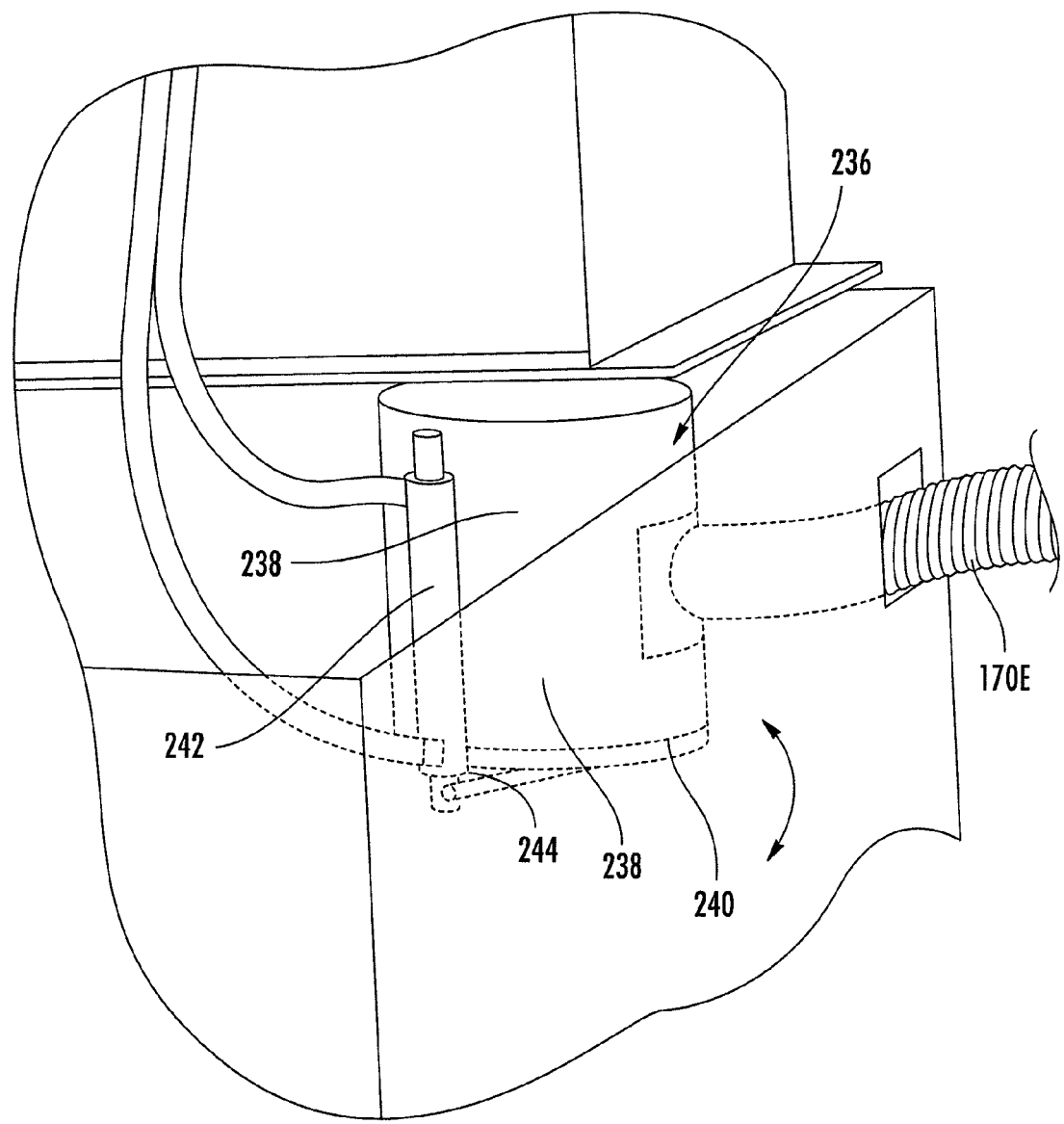
Figure 16:
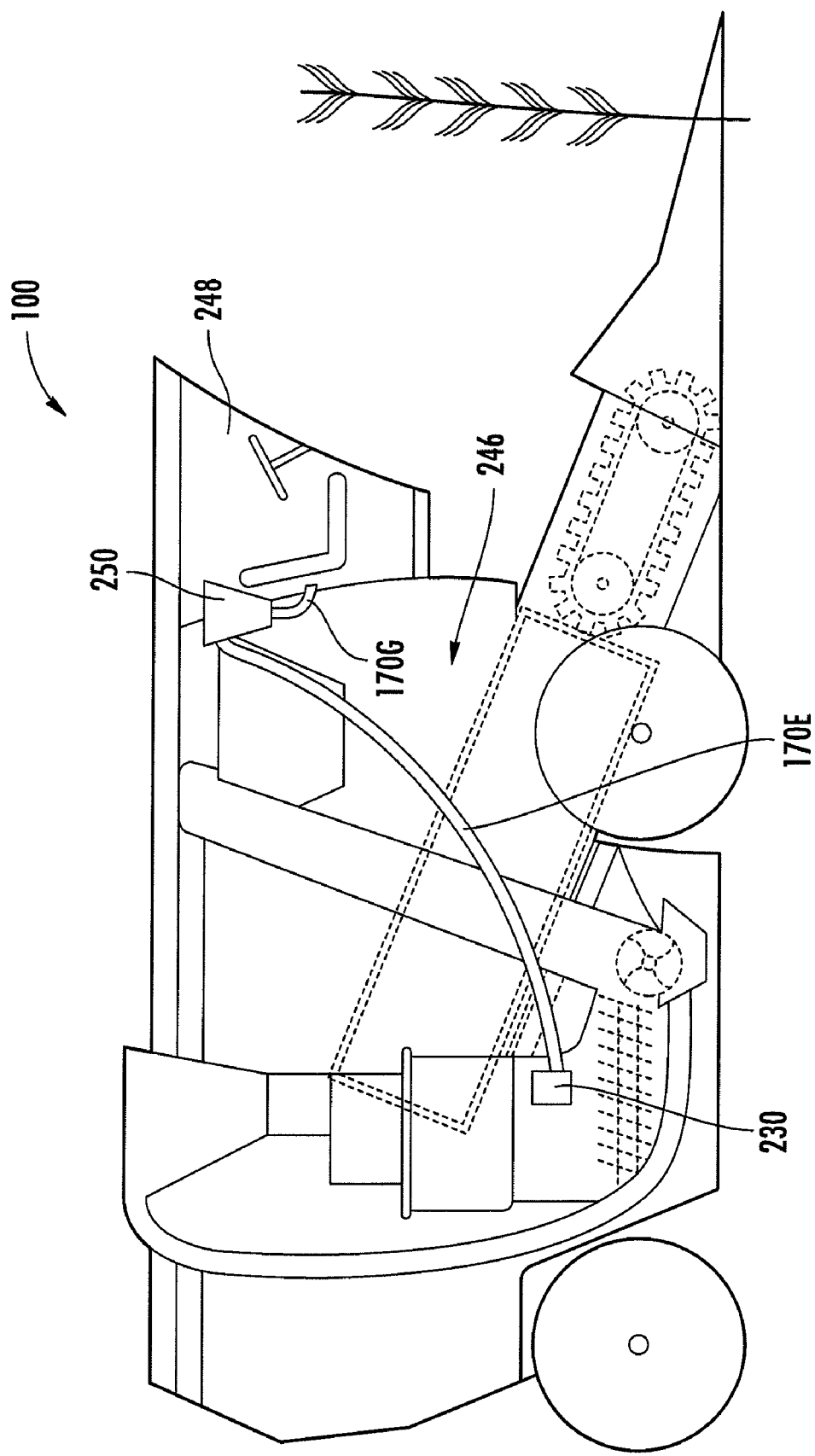
Figure 17:
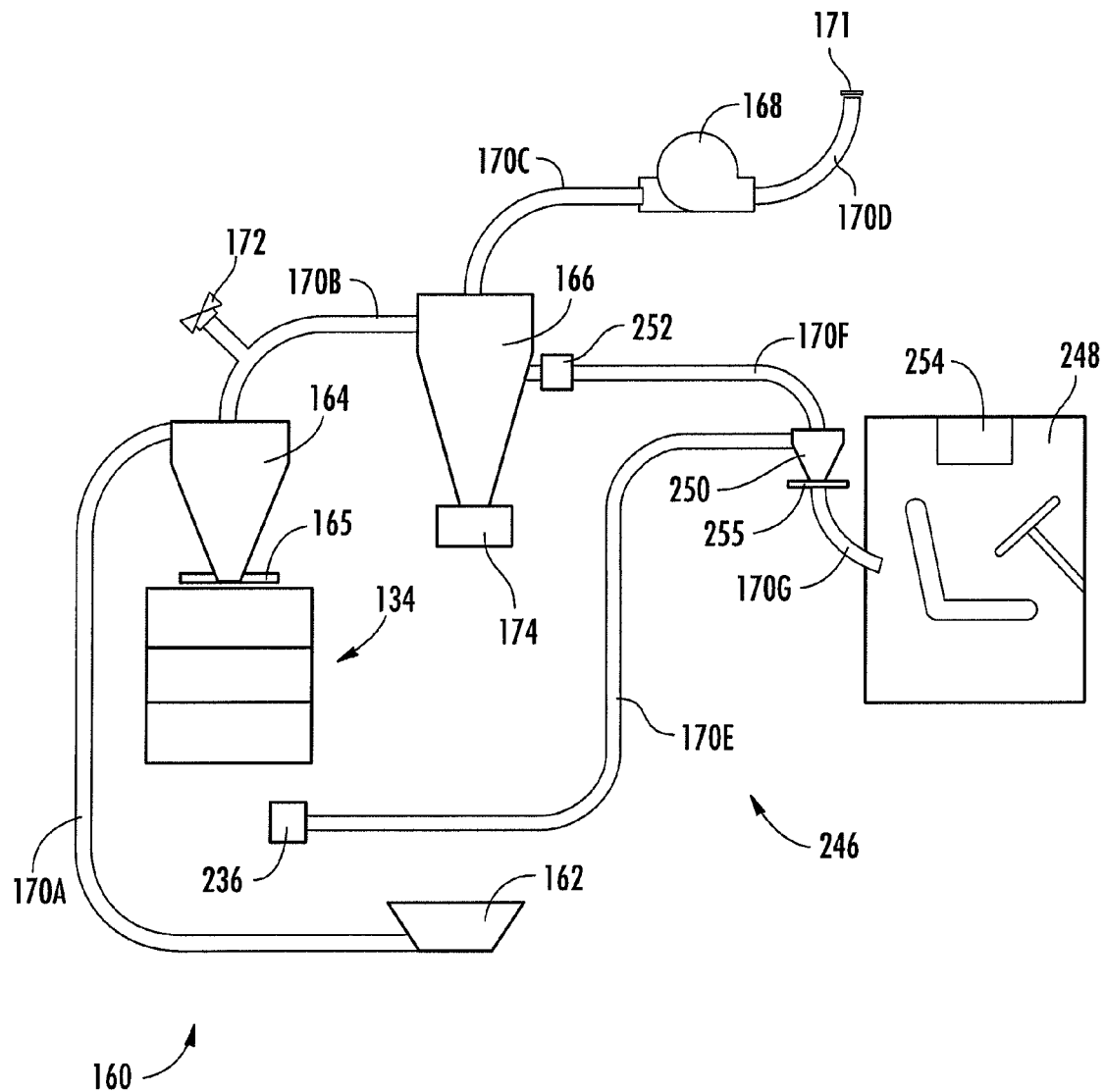

FIG. 8 depicts a perspective view of a moisture test station of a test stage shown in a testing position in accordance with an exemplary embodiment of the present invention;

FIG. 8A depicts a perspective view of the moisture test station of FIG. 8, shown without a side wall in order to depict of some of its internal components in the testing position;

FIG. 9 depicts a perspective view of a moisture test station of a test stage in accordance with an exemplary embodiment of the present invention, shown without a side wall in order to depict some of its internal components in a release position;

FIG. 10 depicts a perspective view of a bulk density station of a test stage shown in a testing position in accordance with an exemplary embodiment of the present invention;

FIG. 11 depicts a perspective view of a bulk density station of a test stage shown with protective shrouds removed to reveal a pair of calibration weights shown in an unloaded position;

FIG. 11A depicts a perspective view shown from another angle of the bulk density station of FIG. 11, wherein the calibration weights are shown in an unloaded position;

FIG. 12 depicts a perspective view of a bulk density station of a test stage shown with protective shrouds removed to reveal a pair of calibration weights shown in the loaded position;

FIG. 12A depicts a perspective view shown from another angle of the bulk density station of FIG. 12, wherein the calibration weights are shown in a loaded position;

FIG. 13 depicts a perspective view of a bulk density station of a test stage shown in a release position in accordance with an exemplary embodiment of the present invention;

FIG. 14 depicts a perspective view of a plot weight station and a discharge hopper of a test stage in accordance with an exemplary embodiment of the present invention;

FIG. 15 depicts a perspective view of a sampling cup in accordance with an exemplary embodiment of the present invention;

FIG. 16 depicts a side schematic view of a combine harvester that includes a sampling cup and a sample delivery system in accordance with an exemplary embodiment of the present invention; and FIG. 17 depicts a schematic view of a test delivery system and a sample delivery system configured to operate under vacuum pressure in accordance with an exemplary embodiment of the present invention.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

The present invention provides a novel combine harvester and associated method configured for gathering grain test data. In general, the combine harvester includes a grain diverting assembly that is configured to selectively divert grain from a grain harvesting path to a grain testing path for the purpose of gathering the grain test data. In various embodiments, the present invention may return the tested grain to the grain harvesting path for further delivery to a primary grain hopper. The present invention may also provide a sampling cup and sample delivery system that allows a sample of the diverted grain to be automatically gathered and delivered to a combine harvester operator.

FIG. 1 depicts a side schematic view of a combine harvester 100 in accordance with an exemplary embodiment of the present invention. The combine harvester 100 of the depicted embodiment includes a removable header 102, a threshing assembly 104, a grain delivery assembly 106, and a primary grain hopper 108. In the depicted embodiment, the combine harvester 100 includes a two row header 102 that is configured for use in a research crop field that includes corn crops. In various other embodiments, however, a variety of headers may be used such as, for example, various headers configured for use with a single row, or a plurality of rows of crops. In addition, although the header of the depicted embodiment is configured for use in harvesting corn, in various embodiments a variety of headers may be used that are configured for harvesting one or more other crops (including, but not limited to, corn, soybeans, canola, wheat, oat, rye, alfalfa, barley, rice, and sunflowers).

In various embodiments the threshing apparatus 104 may have a variety of configurations as are known in the art. In the depicted embodiment, the threshing apparatus 104 is an axial-flow threshing apparatus that includes an in-feed mechanism 110 that comprises a pair of rotating wheels 112 around which a chain 114 is wrapped that carries a series of elongate bars 116 configured to transfer the cut crop material into a threshing rotor 118 that is mounted axially within the combine harvester 100. A rotor housing 120 substantially surrounds the threshing rotor 118 and comprises an arrangement of relatively small openings. A moving sieve 122 is positioned below the threshing rotor 118 and a grain pan 124 is positioned below the moving sieve 120 such that grain separated from non-grain crop material is collected in the grain pan 124. In some embodiments, a fan may be included that is configured to blow air across the grain so as to separate lighter non-grain crop material from the grain before the grain is collected in the grain pan 124. In some embodiments, the lighter non-grain material may be mixed with the larger non-grain crop material and may be disposed onto the crop field.

The grain delivery assembly 106 of the depicted embodiment includes a clean grain auger 126 and a clean grain elevator 128. In the depicted embodiment, the clean grain auger 126 is transversely positioned with respect to the threshing rotor 118 such that the clean grain auger 126 extends across a portion of the width of the combine harvester 100 proximate the bottom of the grain pan 124. In such a manner, the rotating clean grain auger. 126 causes the separated grain from the grain pan 124 to travel to the clean grain elevator 128. In a harvesting operation, the clean grain elevator 128 is configured to transport the separated grain from the grain pan 124 to the primary grain hopper 108. It should be noted that in other embodiments one or more of the clean grain auger 126 and the clean grain elevator 128 could be replaced with another device or system configured to transport the grain. Such devices or systems may include, for example, vacuum transport systems.

Although in various embodiments a variety of threshing and grain delivery assemblies are possible, in the depicted embodiment, the threshing rotor 118, moving sieve 122, clean grain auger 126, and clean grain elevator 128 are mechanically actuated via a belt and pulley system driven by the combine engine 130 so as to associate the speed of the moving sieve 122, clean grain auger 126, and clean grain elevator 128 with the speed of the combine engine 130.

Advantageously, the combine harvester 100 of the depicted embodiment also includes a grain diverting assembly 132 located proximate an interface between the clean grain auger 126 and the clean grain elevator 128. As will be described in more detail below, the grain diverting assembly 132 is configured to switch between a harvest position and a diverted position (and vice versa) so as to selectively divert grain from a harvesting path to a grain testing path. When the grain follows the harvesting path, the grain travels from the grain pan 124 to the primary grain hopper 108 via the clean grain auger 126 and clean grain elevator 128. When the grain is diverted along the grain testing path, the grain travels to a test stage 134, which is configured to gather grain test data.

FIG. 2 depicts a side schematic view of various components of the combine harvester showing a portion of a harvesting path 146 and a grain testing path 148 in accordance with an exemplary embodiment of the present invention. In various embodiments, the test stage 134 may include one or more testing stations configured to gather grain test data. Although in other embodiments a variety of other grain test data may be gathered and the test stage may include any number of testing stations, in the depicted embodiment the test stage 134 includes three test stations: a moisture test station 136, a bulk density station 138, and a plot weight station 140. In the depicted embodiment, the diverted grain follows the grain testing path 148 sequentially through the testing stations—first the moisture test station 136, then the bulk density station 138, and finally the plot weight station 140. After leaving the plot weight station 140, the diverted grain is received into a discharge hopper 142. It should be noted that in other embodiments, the test stage 134 may include more or less test stations and the diverted grain may be presented to the test station(s) in any order.

The discharge hopper 142 of the depicted embodiment includes a discharge auger 144 (shown schematically in FIG. 1) configured to direct the diverted grain from the discharge hopper 142 to the clean grain elevator 128. Once reaching the clean grain elevator 128, the diverted grain rejoins the harvesting path 146 where it is mechanically transported by the clean grain elevator 134 to the primary grain hopper 108. It should be noted that although in the depicted embodiment the diverted grain rejoins the harvesting path 146, in other embodiments the diverted grain may be handled in another manner. For example, in some embodiments the diverted grain may be directed to a secondary hopper. In some other embodiments, any portion or all of the harvested grain and/or any portion or all of the diverted grain may be delivered to a device for processing. In various embodiments, the additional device may be carried by the combine and may comprise a device or a combination of devices configured to handle, treat, and/or manipulate the harvested and/or diverted grain in a desired manner. For example, in some embodiments the diverted grain may be delivered to a grinding device carried by the combine and configured to grind the diverted grain into many small pieces. In some embodiments, the ground grain may then be disposed onto the plot field.

FIGS. 3, 4, and 4A depict various components of the grain diverting assembly 132 shown in a harvest position in accordance with an exemplary embodiment of the present invention. In particular, FIG. 3 depicts a front section view of the grain diverting assembly 132, grain pan 124, clean grain auger 126, and clean grain elevator 128 shown in the harvest position. In the depicted embodiment, the grain diverting assembly 132 includes at least a transfer tube 150, a rotating sleeve 152, and a gate 154 having a pair of sliding plates 155A, 155B (see FIG. 4). As shown, the clean grain auger 126 extends from the bottom of the grain pan 124 through the transfer tube 150 and proximate a lower end of the clean grain elevator 128. The rotating sleeve 152 of the depicted embodiment is configured to rotate about an outer periphery of the transfer tube 150. In the depicted embodiment, the transfer tube 150 includes a cutout portion 156 proximate a bottom portion of the transfer tube 150. In addition, the rotating sleeve 152 of the depicted embodiment also includes a cutout portion 158. FIG. 4 depicts a perspective view of various components of the grain diverting assembly 132 shown in the harvest position, and FIG. 4A depicts a perspective view of the transfer tube 150 and rotating sleeve 152 of the grain diverting assembly 132 shown in the harvest position.

As shown in the figures, in the harvest position the cutout portion 158 of the rotating sleeve 152 is not aligned with the cutout portion 156 of the transfer tube 150 and the gate 154 is open (i.e., plates 155A, 155B do not block the end of the transfer tube 150). In such a manner, grain located in the grain pan 124 follows the harvesting path 146 and is transferred by the clean grain auger 126 through the transfer tube 150 and onto the clean grain elevator 128. Once on the clean grain elevator 128, the grain is transported to the primary grain hopper 108. In various embodiments, the rotating sleeve 152 and the sliding plates 155A, 155B of the diverting assembly gate 154 may be moved to and from the harvest position. Although in various embodiments the rotating sleeve 152 may be moved to and from the harvest position in a variety of ways (such as, for example, via a belt or chain drive system or via an axial drive system that slides the sleeve 152 to and from the harvest position), in the depicted embodiment, the rotating sleeve 152 includes a gear ring 159 which meshes with a pinion gear driven by a motor. In the depicted embodiment, the rotating sleeve 152 is moved to and from the harvest position by controlling the motor to rotate the pinion gear, thus rotating the rotating sleeve 152 around the outer periphery of the transfer tube 150. Although in various embodiments, the sliding plates 155A, 155B may be moved to and from the harvest position in a variety of ways, in the depicted embodiment the sliding plates 155A, 155B are moved to and from the harvest position with a pair of pneumatic pistons, which are attached, respectively, to plates 155A and 155B. The plates 155A, 155B are moved to the harvest position by controlling the pistons to move the plates 155A, 155B apart. In the depicted embodiment, the pinion gear motor and pneumatic pistons are controlled by a central control device, however in other embodiments they may be controlled in a variety of ways, including through independent control devices.

FIGS. 5, 6 and 6A depict various components of the grain diverting assembly 132 shown in a diverted position in accordance with an exemplary embodiment of the present invention. In the diverted position, the cutout portion 158 of the rotating sleeve 152 is substantially aligned with the cutout portion 156 of the transfer tube 150 and the gate 154 is closed (i.e., plates 155A, 155B block the end of the transfer tube 150) so that grain located in the grain pan 124 follows the testing path 148 and is transferred by the clean grain auger 126 through the transfer tube 150 and into the test receptacle 162. As will described in more detail below, once in the test receptacle 162 the grain may be transported to the test stage 134. In various embodiments, the rotating sleeve 152 may be moved to and from the diverted position, and the sliding plates 155A, 155B of the diverting assembly gate 154 may be moved to and from the diverted position. Although in various embodiments the rotating sleeve 152 may be moved to and from the diverted position in a variety of ways, in the depicted embodiment the rotating sleeve 152 is moved to and from the diverted position by controlling the aforementioned pinion gear motor to rotate the pinion gear, thus rotating the rotating sleeve 152 around the outer periphery of the transfer tube 150. It should be noted that although in the depicted embodiment the rotating sleeve 152 rotates about an outer periphery of the transfer tube 150, in other embodiments the rotating sleeve 152 may be located within the transfer tube 150 and thus may rotate within the transfer tube 150. In addition, although in various embodiments, the sliding plates 155A, 155B may be moved to and from the diverted position in a variety of ways (such as, for example, via a gear drive system or via a belt or chain drive system), in the depicted embodiment the plates 155A, 155B are moved to the diverted position by controlling the aforementioned gate pistons to move the plates 155A, 155B together. In the depicted embodiment, the diverter gate 154 includes an opening 161 created when plates 155A, 155B are in the diverted position to accommodate the shaft of the clean grain auger 126, which extends into the clean grain elevator 128. In other embodiments, such as those where the clean grain auger shaft does not extend into the clean grain elevator, the diverter gate 154 may not include such an opening 161.

When the grain diverting assembly 132 is in the diverted position, grain may be collected in the test receptacle 162 and delivered to the test stage 134. In the depicted embodiment, the diverted grain is transported to the test stage 134 via a test delivery system 160 operating under vacuum pressure. Although in other embodiments the diverted grain may be transported to the test stage 134 in any manner (including, for example, through mechanical means), by utilizing vacuum pressure, the diverted grain may be quickly transported to the test stage 134 to allow testing to begin with minimal delay.

Although not intending to be bound by any particular theory, the inventors of the present invention have found that by placing a grain diverting assembly proximate an interface between the clean grain auger 126 and the clean grain elevator 128 and by conveying grain along the harvesting path 146 to the primary grain hopper 146 through mechanical means (such as, for example, via the clean grain auger 126 and clean grain elevator 128) and by conveying grain along the testing path 148 to the test stage 134 through vacuum pressure, the combine harvester 100 of the present invention may be operated at a faster pace and thus may process more crop material in a shorter period of time.

FIG. 7 depicts a schematic view of a test delivery system 160 configured to operate under vacuum pressure in accordance with an exemplary embodiment of the present invention. Although in other embodiments, the test delivery system may have a variety of configurations, in the depicted embodiment, the test delivery system 160 includes the test receptacle 162, a test cyclone 164, a dust cyclone 166, and a vacuum device 168. The vacuum device 168 of the depicted embodiment is a blower device, which creates the negative pressure in the system 160. In the depicted embodiment, the test receptacle 162 is connected to the test cyclone 164 via a tube 170A, the test cyclone 164 is connected to the dust cyclone 166 via a tube 170B, the dust cyclone 166 is connected to the vacuum device 168 via a tube 170C, and the vacuum device 168 expels air to the atmosphere via tube 170D, which includes a muffler device 171 on an end thereof.

In general, the test delivery system 160 of the depicted embodiment is configured to operate as follows: A gate 165 comprising a sliding release plate is located proximate the bottom of the test cyclone 164 and is closed to maintain negative pressure through the system 160. Vacuum pressure generated by vacuum device 168 causes diverted grain from the test receptacle 162 to be pulled into the test cyclone 164 through tube 170A. In the depicted embodiment, the test cyclone 164 is configured to collect the transported grain proximate the bottom of the test cyclone 164 while tube 170B carries effluent "dirty air" to the dust cyclone 166. The dust cyclone 166 is configured to receive the dirty air and to collect dust particles in a dust tank 174 proximate the bottom of the dust cyclone 166, while effluent cleaner air travels via tube 170C through the vacuum device 168. In the depicted embodiment, the dust cyclone 166 also includes a filter located inside the cyclone 166. The vacuum device 168 expels the air through tube 170D and to the atmosphere. As will be described in more detail below, in the depicted embodiment a butterfly valve 172 is included in tube 170B to allow quick venting of the test delivery system 160. (It should be noted that to simplify FIGS. 1 and 2, various components of the test delivery system 160 are not shown, including the dust cyclone 166, vacuum device 168, butterfly valve 172, dust tank 164, and associated tubes 170B-D.)

Once the diverted grain to be tested is collected in the test cyclone 164, the grain is released to the test stage 134. In the depicted embodiment, the grain is released to the test stage 134 by opening the butterfly valve 172 and opening the test cyclone gate 165. In the depicted embodiment, the test cyclone gate 165 and the butterfly valve 172 are opened via respective pneumatic pistons controlled by the central control device, however in other embodiments the test cyclone gate 165 and the butterfly valve 172 may be opened or controlled in a variety of ways, include through independent control devices. By opening the butterfly valve 172, this quickly relieves the pressure in the system 160 and allows the diverted grain to flow down into the test stage 134. In various embodiments the test cyclone gate 165 may be controlled to release any amount of the diverted grain from the test cyclone 164 into the first station of the test stage 134. In the depicted embodiment, the first station of the test stage 134 is the moisture test station 136.

FIG. 8 depicts a perspective view of a moisture test station 136 in accordance with an exemplary embodiment of the present invention. Although in various embodiments, a moisture test station may have a variety of configurations, in the depicted embodiment, the moisture test station 136 generally includes a moisture test container 176, a moisture sensor 178, and a gate 180 comprising a sliding release plate 182. The moisture test station 136 of the depicted embodiment is configured operate in a testing position, in which moisture data is gathered from a portion of the diverted grain, and a release position, in which diverted grain is released along the testing path 148 to the next station of the test stage 134. FIG. 8A depicts a perspective view of the moisture test station of FIG. 8, shown with a side wall of the moisture test container 176 removed in order to depict of some of its internal components in the testing position. FIG. 9 depicts a perspective view of the moisture test station 136 with a side wall removed in order to depict some of its internal components in a release position. In the testing position, gate 180 is closed such that the release plate 182 covers an opening 184 at the bottom of the moisture test container 176. Although in various embodiments the components of the moisture test station 136 may be moved between the testing position and the release position in a variety of ways, in the depicted embodiment a pneumatic piston 185 moves the moisture test station 136 between the testing position and the release position. In the depicted embodiment, the pneumatic piston 185 is controlled by the central control device, however in other embodiments it may be controlled in a variety of ways, including through an independent control device.

Referring to FIG. 8A, the pneumatic piston 185 of the depicted embodiment is connected to the sliding release plate 182 and a sliding vertical plate 186. A rotating directing plate 188 rests on top of the sliding vertical plate 186, such that sliding movement of the vertical plate 186 rotates the directing plate 188 about a rotating end 190. Thus, in the testing position diverted grain received into the moisture test container 176 is directed toward the moisture sensor 178, which extends into a portion of the moisture test container 176. In addition, the moisture test container 176 includes a pair of stationary directing blocks 183A, 183B which further act to direct diverted grain received by the moisture test container 176 toward the moisture sensor 178. It should be noted that in other embodiments a variety of configurations are possible for a moisture test station, including embodiments that do not include directing members. In some embodiments, vertical plate 186 is stationary and does not slide. In such embodiments, there is no mechanism that attaches plate 186 to gate 180 in order to effect sliding.

Referring to FIG. 9, in the release position the pneumatic piston 185 moves the sliding release plate 182 and the sliding vertical plate 186 in a direction that unblocks the opening 184 as shown. As the sliding vertical wall 186 travels in the movement direction, the directing plate 188 rotates about the rotating end 190 to open a path through the moisture testing station 136. In such a manner, the diverted grain in the moisture station 136 (and/or any grain remaining in the test cyclone 164) may travel through the moisture test station 134 along the testing path 148 and into the next station of the test stage 134. In various embodiments, the moisture testing station gate 180 may be controlled to release any amount of the diverted grain into the next station of the test stage 134. The moisture testing station gate 180 of the depicted embodiment is controlled to allow all of the diverted grain to travel to the next station of the test stage 134. In the depicted embodiment, the next station of the test stage 134 is the bulk density station 138.

FIG. 10 depicts a perspective view of a bulk density station 138 in accordance with an exemplary embodiment of the present invention. Although in various embodiments, a bulk density station may have a variety of configurations, in the depicted embodiment the bulk density station 138 generally includes a bulk density cup 192 comprising a cup body 194 and first and second cup axles 196A, 196B that extend opposite each other from the cup body 194, and a pair of load measuring devices 198A, 198B (see FIG. 11A) that support the respective cup axles 196A, 196B.

Although in various embodiments bulk density data may be gathered in a variety of ways, in the depicted embodiment the bulk density cup 192 is configured to rotate between a testing position, in which bulk density data is gathered from a received portion of the diverted grain, and a release position, in which diverted grain is released along the testing path 148 to the next station of the test stage 134. In various embodiments, the bulk density data may represent an independent measurement. In other embodiments, the bulk density data may be combined with other data to generate another form of measurement. For example, in some embodiments the bulk density data for the received grain may be combined with the moisture data to generate test weight data.

The bulk density cup 192 of FIG. 10 is shown in a testing position (i.e., upright) so as to receive into the cup body 194 at least a portion of the diverted grain released by the moisture test station 136 and/or the test cyclone 164. In some embodiments, the moisture test station 136 and/or the test cyclone 164 may be controlled to release only a portion of the diverted grain into the bulk density station 138. In other embodiments, the moisture test station 136 and/or the test cyclone 164 may be controlled to release all of the diverted grain into the bulk density station 138.

The load measuring devices 198A, 198B of the depicted embodiment are configured to measure the load of the bulk density cup 192 when it is full of grain. Because the bulk density measurement of the depicted embodiment is a function of the volume of grain received into the cup body 194, the bulk density station 138 of the depicted embodiment also includes a scraper 200 that is configured to sweep across a top plane of the bulk density cup 192 so as to remove any excess amount of diverted grain and to ensure that the bulk density cup 192 includes a predetermined volume of grain therein. Although in various embodiments the scraper 200 may be swept across the top plane of the bulk density cup 192 in a variety of ways, in the depicted embodiment a pneumatic piston 202 moves a rocker arm 204 to rotate the scraper 200 about a pivot axis 205. In the depicted embodiment, the scraper 200 includes a support bar 206 and a flexible member 208 (see FIG. 11), such as a spring, that is configured to absorb minor surface inconsistencies of the plurality of grain contained in the bulk density cup 192 as the scraper 200 sweeps across the top plane of the bulk density cup 192. In the depicted embodiment, the pneumatic piston 202 is controlled by the central control device, however in other embodiments it may be controlled in a variety of ways, including through an independent control device.

In the depicted embodiment, the bulk density station 138 also includes a function that allows for the load measuring devices 198A, 198B to be automatically calibrated. In such a manner, the bulk density cup 192 may be loaded with a known load that may be measured with the load measuring devices 198A, 198B so that the controller may automatically compensate for any load measuring variations. FIG. 11 depicts a perspective view of the bulk density station 138 with protective shrouds 199A, 199B removed to reveal a pair of calibration weights 210A, 210B that are configured to be used for the automatic calibration function. Although in various embodiments the bulk density cup 192 may be calibrated in a variety ways, in the depicted embodiment the calibration weights 210A, 210B each include a cutout portion 212A, 212B that allows the weights 210A, 210B to be lowered onto the respective cup axles 196A, 196B, proximate the respective load measuring devices 198A, 198B. FIG. 11A depicts a perspective view shown from another angle of the bulk density station 138. Although in various embodiments the calibration weights 210A, 210B may be lowered onto the respective cup axles 196A, 196B in a variety of ways, in the depicted embodiment respective pneumatic pistons 214A, 214B move the calibration weights 210A, 210B from an unloaded position to a loaded position by rotating respective rocker arms 216A, 216B about respective pivot axes 218A, 218B such that the calibration weights 210A, 210B move downward as the rocker arm 216A, 216B rotates. In FIGS. 11 and 11A, the calibration weights 210A, 210B, pneumatic pistons 214A, 214B, and rocker arms 216A, 216B are shown in an unloaded position. In FIGS. 12 and 12A, the calibration weights 210A, 210B, pneumatic pistons 214A, 214B, and rocker arms 216A, 216B are shown in a loaded position.

FIG. 13 depicts a perspective view of the bulk density station 138 shown in a release position in accordance with an exemplary embodiment of the present invention. Although in various embodiments the bulk density cup 192 may be moved between the testing position and the release position in a variety of ways, in the depicted embodiment a pneumatic piston 220 rotates a rocker arm 222 that slides inside a crank arm 224, which is fixedly attached to one of the cup axles 196A (see FIG. 12A). As a result, the bulk density cup 192 may be rotated between the testing position and the release position (and vice versa). In the depicted embodiment, the pneumatic piston 220 is controlled by the central control device, however in other embodiments it may be controlled in a variety of ways, including through an independent control device.

In the release position, the bulk density cup 192 is rotated into an inverted position so that grain located in the cup body 194 is released along the testing path 148 into the next station of the test stage 134. Although in various embodiments the bulk density cup 192 may have a variety of configurations, the cup body 194 of the depicted embodiment has a substantially cylindrical main body shape with a conical bottom portion. As such, when the bulk density cup 192 of the depicted embodiment is rotated into the release position, any grain that falls over the cup 192 will be deflected into the next station and will not be captured by the cup 192. In the depicted embodiment, the next station of the test stage 134 is the plot weight station 140.

FIG. 14 depicts a perspective view of the plot weight station 140 and the discharge hopper 142 in accordance with an exemplary embodiment of the present invention. Although in various embodiments, a plot weight station may have a variety of configurations, the plot weight station 140 of the depicted embodiment comprises a plot weight container 226 that is supported on four corners by respective load measuring devices 228A, 228B, 228C, 228D. It should be noted that in some embodiments, the moisture test station 136 and/or the test cyclone 164 may be controlled to release only a portion of the diverted grain through the bulk density station 138 and into the plot weight station 140. However, in the depicted embodiment the moisture test station 136 and/or the test cyclone 164 are controlled to release all of the diverted grain into the plot weight station 140. In such a manner, all of the diverted grain (which in the depicted embodiment may represent a plot's worth of grain) is received into the plot weight container 226 so that the weight of the diverted grain may be gathered.

As similarly described above with respect to the bulk density station 136, in some embodiments the plot weight station 140 may additionally be configured for automatic calibration. In such embodiments, the plot weight container 226 may be loaded with a known load and the load measuring devices 228A, 228B, 228C, and 228D may be used to measure the load so that the controller may automatically compensate for any load measuring variations.

The plot weight station 140 of the depicted embodiment also includes a gate 230 that is configured to move between a testing position and a release position. In the testing position, the gate 230 is closed such that any grain received in the plot weight container 226 remains in the container 226. In the release position, the grain contained in the plot weight container 226 is released along the testing path 148 and into the discharge hopper 142. Although in various embodiments the diverted grain may be released from the plot weight container 226 into the discharge hopper 142 in a variety of ways, in the depicted embodiment a pneumatic piston 232 moves an actuation mechanism 234, which opens a pair of panels disposed proximate the bottom of the plot weight container 226. In the depicted embodiment, the piston 232 is controlled by a central control device, however in other embodiments the piston 232 may be controlled in a variety of ways, including through an independent control device.

The discharge hopper 142 of the depicted embodiment includes a mechanical discharge auger 144 (shown schematically in FIG. 1) configured to direct the diverted grain along the testing path 148 to the clean grain elevator 128. Once at the clean grain elevator 128, the diverted grain rejoins the harvesting path 146 where it is mechanically transported by the clean grain elevator 128 to the primary grain hopper 108. In the depicted embodiment, the discharge auger 144 is mechanically powered via a belt and pulley system driven by the combine engine so as to associate the speed of the discharge auger 144 with the speed of the other mechanical elements of the combine 100, including, for example, the clean grain elevator 128.

In various embodiments, it may be also desirable to obtain a sample of the diverted grain. For instance, it may be desirable to obtain a sample of diverted grain so that additional testing of the diverted grain may be performed or so that the grain test data gathered by the test stage 134 may be verified through independent testing, such as, for example, through controlled lab tests. FIG. 15 depicts a perspective view of a sampling cup 236 in accordance with an exemplary embodiment of the present invention. In the depicted embodiment, the sampling cup 236 comprises a cup body 238 and a movable base 240, which is configured to move between a sampling position and an open position. In the depicted embodiment, the sample cup 236 is located along the grain testing path 148 and is configured, when in a sampling position, to receive a sample portion of the diverted grain. Although in various embodiments the sampling cup 236 may be placed in other positions, in the depicted embodiment the sampling cup 236 is located below the plot weight station 140, inside of the discharge hopper 142. As such, when the diverted grain is released from the plot weight container 226, a portion of the grain may be received in the sampling cup 236.

In the sampling position, the movable base 240 of the sampling cup 236 rests up against the cup body 238 to enable the sampling cup 236 to receive at least a portion of the diverted grain traveling along the testing path 148. In FIG. 15, the movable cup base 240 of the sampling cup 236 is shown in a sampling position. In the open position, the movable base 240 moves away from the cup body 238. In such a manner, diverted grain may travel through the sampling cup 236 without being received therein. Although in various embodiments the movable base 240 may be moved in a variety of ways, in the depicted embodiment the movable base is moved with a pneumatic piston 242, which is attached to the base 240 such that when the piston actuates, the base 240 rotates about a pivot axis 244.

In various embodiments, once a sample has been received it may be further desirable to deliver the sample to a location where a combine operator may gather the sample. As such, a sample delivery system 246 may be included that is configured to deliver the sample portion of diverted grain to a combine operator location. Although in various embodiments, a combine operator may operate the combine from a variety of locations, in the depicted embodiment the combine operator operates the combine from inside an enclosed combine cab 248. FIG. 16 depicts a side schematic view of a combine harvester 100 that includes a sampling cup 236 and various components of a sample delivery system 246 configured to deliver a sample portion of diverted grain directly into the combine cab 248. Although in other embodiments the sample portion of grain may be transported to the operator location in any manner (including, for example, through mechanical means), in the depicted embodiment the sample delivery system 246 operates under vacuum pressure.

FIG. 17 depicts a schematic view of the test delivery system 160 and the sample delivery system 246 configured to operate under vacuum pressure in accordance with an exemplary embodiment of the present invention. Although in other embodiments, the test delivery system 160 and/or the sample delivery system 246 may have a variety of configurations, as noted above in the depicted embodiment the test delivery system 160 includes the test receptacle 162, the test cyclone 164, the dust cyclone 166, the vacuum device 168, and tubes 170A-170D. The sample delivery system 246 includes the sampling cup 236, a sample cyclone 250, tubes 170E-170G, and a valve mechanism 252, which is attached to the dust cyclone 156 and is configured to selectively generate pressure in the sample delivery system 246. In the depicted embodiment, the sampling cup 236 is connected to the sample cyclone 250 via tube 170E, the sampling cyclone 250 is connected to the valve mechanism 252 via tube 170F, and the sampling cyclone 250 is connected into the combine cab via tube 170G.

In general, the sample delivery system 246 of the depicted embodiment is configured to operate as follows: Operation of the vacuum device 168 generates vacuum pressure in the dust cyclone 166 of the test delivery system 160. Valve mechanism 252 is attached to the dust cyclone 166 such that the valve device 252 may be actuated to also generate vacuum pressure in the sample delivery system 246. A sliding release gate 255 comprised of a plate is located proximate the bottom of the sampling cyclone 250 and is closed to maintain negative pressure through the system 246. As such, when the sampling cup 236 is in a sampling position and has received a sample portion of the diverted grain, and once the valve mechanism 252 has been actuated, the sample portion of diverted grain is pulled from the sampling cup 236 into the sampling cyclone 250. In the depicted embodiment, the sampling cyclone 250 is configured to collect the transported sample portion of grain proximate the bottom of the sampling cyclone 250, while tube 170F carries effluent "dirty air" to the dust cyclone 166. As noted above, the dust cyclone 166 is configured to receive the dirty air and to collect dust particles in a dust tank 174 proximate the bottom of the dust cyclone 166, while the effluent air travels via tube 170C through the vacuum device 168. As noted above, the vacuum device expels the air to the atmosphere via tube 170D, which contains a muffler 171 on an end thereof. (It should be noted that to simplify FIG. 16, various components of the sample delivery system 246 are not shown, including the valve mechanism 252 connected to the dust cyclone 166 and the associated tube 170F.)

Once the sample portion of diverted grain is collected in the sampling cyclone 250, the sample portion of grain may be released into the combine cab 248 where the operator may capture the sample, such as for example, by attaching a bag to the end of the tube 170G. In the depicted embodiment, the sample portion of grain is released into the combine cab 148 by deactivating valve mechanism 252 and opening the sliding release gate 255. In the depicted embodiment, the gate 255 is opened via a pneumatic piston controlled by the central control device, however in other embodiments the gate 255 may be opened or controlled in a variety of ways, including through an independent control device.

In the depicted embodiment, the combine cab 148 also includes a touch screen control panel 254 having a graphical user interface that is configured to allow the operator to control one or more functions of the combine harvester 100, such as, for example, any of the controllable functions of the grain diverting assembly 132, the test delivery assembly 160, the test stage 134, the sampling cup 236, and/or the sample delivery system 246.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A combine harvester configured to selectively gather grain test data, said combine harvester comprising:
    a threshing assembly configured to separate grain from other crop material;
    a grain delivery assembly comprising a clean grain auger and a clean grain elevator, the grain delivery assembly configured to receive grain from the threshing assembly and deliver the grain along a harvesting path to a primary grain hopper; and
    a grain diverting assembly located proximate an interface between the clean grain auger and the clean grain elevator,
    wherein the grain diverting assembly is configured to selectively divert grain from the harvesting path to a grain testing path where at least a portion of the diverted grain is delivered to a test stage configured to gather grain test data.

2. The combine harvester of claim 1, wherein the clean grain auger receives the grain from the threshing assembly and the clean grain elevator delivers the grain to the primary grain hopper.

3. The combine harvester of claim 2, wherein the grain diverting assembly comprises:
    a transfer tube through which grain is transported from the threshing assembly by the clean grain auger, the transfer tube including a cutout located on a bottom portion thereof;
    a gate located between the transfer tube and the clean grain elevator configured to be positioned in a harvest position and a diverted position; and
    a rotating sleeve configured rotate about an outer periphery of the transfer tube, the rotating sleeve also including a cutout portion configured to be positioned in a harvest position and a diverted position,
    wherein in the harvest position, the gate is open and the transfer tube cutout and the sleeve cutout are not aligned so that grain transported from the threshing assembly is delivered to the clean grain elevator, and wherein in the diverted position the gate is closed and the transfer tube cutout and the sleeve cutout are substantially aligned so that grain transported from threshing assembly is delivered to the test stage.

4. The combine harvester of claim 1, further comprising a test delivery system configured to deliver the diverted grain to the test stage.

5. The combine harvester of claim 4, wherein the test delivery system utilizes vacuum pressure to deliver the diverted grain to the test stage.

6. The combine harvester of claim 5, wherein the test delivery system includes a test grain cyclone and a dust collection cyclone.

7. The combine harvester of claim 1, wherein the test stage comprises at least one of a moisture test station, a bulk density station, and a plot weight station.

8. The combine harvester of claim 7, wherein the test stage comprises at least a bulk density station and wherein the bulk density station includes a bulk density cup supported by at least one load measuring device.

9. The combine harvester of claim 8, wherein the bulk density station further includes a scraper device configured to sweep across a top plane of the bulk density cup to remove any excess amount of diverted grain and to ensure that the bulk density cup includes a predetermined volume of grain therein.

10. The combine harvester of claim 8, wherein the bulk density station further includes at least one calibration weight configured to load the bulk density cup with a known load, and further comprising a control device configured to automatically load the bulk density cup with the calibration weight to calibrate the load measuring device.

11. The combine harvester of claim 8, wherein the bulk density station includes a rotatable bulk density cup comprising a cup body and first and second cup axles extending opposite each other from the cup body, and wherein the first and second cup axles are supported by respective first and second load measuring devices.

12. The combine harvester of claim 11, wherein the bulk density station further includes respective first and second calibration weights configured to load the first and second cup axles with a known load, and wherein the combine harvester further comprises a control device configured to automatically load the first and second cup axles with the first and second calibration weights to calibrate the first and second load measuring devices.

13. The combine harvester of claim 7, wherein the test stage comprises at least a plot weight station and wherein the plot weight station includes a plot weight hopper supported by at least one load measuring device.

14. The combine harvester of claim 13, wherein the plot weight station further includes at least one calibration weight configured to load the plot weight hopper with a known load, and further comprising a control device configured to automatically load the plot weight hopper with the calibration weight to calibrate the load measuring device.

15. A combine harvester configured to selectively gather grain test data, said combine harvester comprising:
a threshing assembly configured to separate grain from other crop material;
a grain delivery assembly configured to receive grain from the threshing assembly and deliver the grain along a harvesting path to a primary grain hopper; and
a grain diverting assembly,
wherein the grain diverting assembly is configured to selectively divert grain from the harvesting path to a grain testing path where at least a portion of the diverted grain is delivered to a test stage configured to gather grain test data, and
wherein the combine harvester includes a combine operator location and further comprises:
a sampling cup located within the grain testing path, the sampling cup configured to receive a sample portion of the diverted grain; and
a sample delivery system configured to deliver the sample portion of diverted grain to the combine operator location.

16. The combine harvester of claim 15, wherein the sample delivery system utilizes vacuum pressure to deliver the sample portion of the diverted grain to the combine operator location.

17. The combine harvester of claim 16, wherein the sample delivery system includes a sample cyclone.

18. A method of selectively gathering grain test data using a combine harvester having a threshing assembly, a primary grain hopper, and a grain delivery assembly comprising a clean grain auger and a clean grain elevator, said method comprising:
separating grain from other crop material using the threshing assembly;
receiving grain from the threshing assembly and delivering the grain along a harvesting path to the primary grain hopper using the grain delivery system;
selectively diverting grain from the harvesting path to a grain testing path using a diverting assembly located proximate an interface between the clean grain auger and the clean grain elevator;
delivering at least a portion of the diverted grain to a test stage of the combine harvester; and
gathering grain test data using the test stage.

19. The method of claim 18, wherein receiving grain from the threshing assembly and delivering the grain along a harvesting path to the primary grain hopper comprises receiving the grain from the threshing assembly with the clean grain auger and delivering the grain to the primary grain hopper with the clean grain elevator.

20. The method of claim 19, further comprising:
transporting grain from the threshing assembly through a transfer tube using the clean grain auger, the transfer tube including a cutout located on a bottom portion thereof; and
positioning a gate located between the transfer tube and the clean grain elevator in a harvest position and a diverted position and positioning a cutout of a rotating sleeve in a harvest position and a diverted position,
wherein in the harvest position, the gate is positioned open and the rotating sleeve is positioned so that the rotating sleeve cutout is not aligned with the transfer tube cutout and grain is transported from the threshing assembly to the clean grain elevator, and wherein in the diverted position the gate is positioned closed and the rotating sleeve is positioned so that the rotating sleeve cutout is substantially aligned with the transfer tube cutout and grain is transported from threshing assembly to the test stage.

21. The method of claim 18, further comprising delivering the diverted grain to the test stage using a test delivery system.

22. The method of claim 21, wherein the test delivery system utilizes vacuum pressure to deliver the diverted grain to the test stage.

23. The method of claim 22, wherein the test delivery system includes a test grain cyclone and a dust collection cyclone.

24. The method of claim 18, wherein the test stage comprises at least one of a moisture test station, a bulk density station, and a plot weight station.

25. The method of claim 24, wherein the test stage comprises at least a bulk density station and wherein the bulk density station includes a bulk density cup supported by at least one load measuring device.

26. The method of claim 25, further comprising sweeping a scraper device across a top plane of the bulk density cup to remove any excess amount of diverted grain and to ensure that the bulk density cup includes a predetermined volume of grain therein.

27. The method of claim 25, further comprising using a control device to automatically load the bulk density cup with at least one calibration weight of a known load, and calibrating the load measuring device with the control device.

28. The method of claim 25, wherein the bulk density station includes a rotatable bulk density cup comprising a cup body and first and second cup axles extending opposite each other from the cup body, and wherein the first and second cup axles are supported by respective first and second load measuring devices.

29. The method of claim 28, further comprising using a control device to automatically load the first and second axles of the bulk density cup with respective first and second calibration weights of known loads, and calibrating the first and second load measuring devices with the control device.

30. The method of claim 24, wherein the test stage comprises at least a plot weight station and wherein the plot weight station includes a plot weight hopper supported by at least one load measuring device.

31. The method of claim 30, further comprising using a control device to automatically load the plot weight hopper with at least one calibration weight of a known load, and calibrating the load measuring device with the control device.

32. A method of selectively gathering grain test data using a combine harvester having a threshing assembly, a primary grain hopper, and a grain delivery assembly, said method comprising:
    separating grain from other crop material using the threshing assembly;
    receiving grain from the threshing assembly and delivering the grain along a harvesting path to the primary grain hopper using the grain delivery system;
    selectively diverting grain from the harvesting path to a grain testing path using a diverting assembly;
    delivering at least a portion of the diverted grain to a test stage of the combine harvester; and
    gathering grain test data using the test stage,
    further comprising:
    receiving a sample portion of the diverted grain in a sampling cup located within the grain testing path; and
    delivering the sample portion of diverted grain to a combine operator location of the combine harvester.

33. The method of claim 32, wherein the sample delivery system utilizes vacuum pressure to deliver the sample portion of the diverted grain to the combine operator location.

34. The method of claim 33, wherein the sample delivery system includes a sample cyclone.

\* \* \* \* \*